US008911357B2

(12) United States Patent
Omori

(10) Patent No.: US 8,911,357 B2
(45) Date of Patent: Dec. 16, 2014

(54) OPTICAL STRUCTURE OBSERVATION APPARATUS AND STRUCTURE INFORMATION PROCESSING METHOD OF THE SAME

(75) Inventor: Toshihiko Omori, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 882 days.

(21) Appl. No.: 12/642,570

(22) Filed: Dec. 18, 2009

(65) Prior Publication Data

US 2010/0158339 A1 Jun. 24, 2010

(30) Foreign Application Priority Data

Dec. 19, 2008 (JP) ................................ 2008-324607

(51) Int. Cl.
*A61B 1/005* (2006.01)
*A61B 5/00* (2006.01)
*A61B 1/00* (2006.01)

(52) U.S. Cl.
CPC ............ *A61B 5/6852* (2013.01); *A61B 1/00096* (2013.01); *A61B 1/00193* (2013.01); *A61B 5/0084* (2013.01); *A61B 5/0066* (2013.01); *A61B 1/00009* (2013.01); *A61B 1/00133* (2013.01); *A61B 1/00172* (2013.01)
USPC ........... 600/111; 600/101; 600/109; 600/112; 600/407; 600/425; 600/476; 600/478; 356/479; 356/497

(58) Field of Classification Search
USPC ........... 382/131, 128; 351/206; 356/497, 479; 600/109, 111, 112, 407, 425, 476, 478
See application file for complete search history.

(56) References Cited

U.S. PATENT DOCUMENTS

| | | | | | |
|---|---|---|---|---|---|
| 4,516,261 | A | * | 5/1985 | Harding et al. | ............... 382/131 |
| 5,524,130 | A | * | 6/1996 | Ohhashi | ......................... 378/15 |
| 5,921,926 | A | * | 7/1999 | Rolland et al. | ............... 600/407 |
| 5,957,941 | A | * | 9/1999 | Ream | ............................ 606/159 |
| 6,069,698 | A | * | 5/2000 | Ozawa et al. | ................. 356/511 |

(Continued)

FOREIGN PATENT DOCUMENTS

| | | |
|---|---|---|
| EP | 1972271 A1 | 9/2008 |
| JP | 2007-225349 A | 9/2007 |
| JP | 2009-183332 A | 8/2009 |
| WO | WO 2008/039660 A2 | 4/2008 |

OTHER PUBLICATIONS

Qi et al., Journal of Biomedical Optics, "Automated quantification of colonic crypt morphology using integrated microscopy and optical coherence tomography", vol. 13, No. 5, pp. 054055-1 to 054055-11, Sep./Oct. 2008.

(Continued)

*Primary Examiner* — Allen C. Ho
(74) *Attorney, Agent, or Firm* — Birch, Stewart, Kolasch & Birch, LLP

(57) ABSTRACT

In the optical structure observation apparatus according to an aspect of the present invention, a middle layer of a measured object having a layer structure at least including a surface layer and the middle layer is extracted and flattened to be a same flat plane, the optical stereoscopic structure image is reconstructed with the flattened middle layer as the reference layer, the three-dimensional converted optical structure image is generated, and at least the three-dimensional converted optical structure image is imaged and displayed on the display device, whereby the structure information with the middle layer in the measured object having the layer structure as a basal plate can be visually determined.

18 Claims, 21 Drawing Sheets

(56) References Cited

U.S. PATENT DOCUMENTS

| | | | |
|---|---|---|---|
| 6,134,003 A * | 10/2000 | Tearney et al. | 356/479 |
| 6,485,413 B1 * | 11/2002 | Boppart et al. | 600/160 |
| 6,498,948 B1 | 12/2002 | Ozawa et al. | |
| 6,501,551 B1 * | 12/2002 | Tearney et al. | 356/477 |
| 6,527,708 B1 * | 3/2003 | Nakamura et al. | 600/160 |
| 6,668,185 B2 * | 12/2003 | Toida | 600/425 |
| 6,687,010 B1 * | 2/2004 | Horii et al. | 356/479 |
| 6,797,931 B2 * | 9/2004 | Iizuka et al. | 250/201.3 |
| 6,879,851 B2 * | 4/2005 | McNamara et al. | 600/407 |
| 7,158,234 B2 * | 1/2007 | Uchiyama et al. | 356/479 |
| 7,180,600 B2 * | 2/2007 | Horii et al. | 356/479 |
| 7,283,247 B2 * | 10/2007 | Okawa et al. | 356/477 |
| 7,324,211 B2 * | 1/2008 | Tsujita | 356/497 |
| 7,366,376 B2 * | 4/2008 | Shishkov et al. | 385/35 |
| 7,382,949 B2 * | 6/2008 | Bouma et al. | 385/25 |
| 7,450,242 B2 * | 11/2008 | Toida et al. | 356/479 |
| 7,474,407 B2 * | 1/2009 | Gutin | 356/479 |
| 7,539,362 B2 * | 5/2009 | Teramura et al. | 385/12 |
| 7,542,145 B2 * | 6/2009 | Toida et al. | 356/479 |
| 7,544,162 B2 * | 6/2009 | Ohkubo | 600/173 |
| 7,551,817 B2 * | 6/2009 | Teramura | 385/31 |
| 7,576,866 B2 * | 8/2009 | Ohkubo | 356/479 |
| 7,583,385 B2 * | 9/2009 | Kato | 356/479 |
| 7,589,842 B2 * | 9/2009 | Kuroiwa | 356/497 |
| 7,593,626 B2 * | 9/2009 | Kato | 396/17 |
| 7,756,311 B2 * | 7/2010 | Yasuno et al. | 382/128 |
| 7,823,782 B2 * | 11/2010 | Yatagai et al. | 235/454 |
| 7,952,718 B2 * | 5/2011 | Li et al. | 356/479 |
| 7,965,392 B2 * | 6/2011 | Tamura | 356/479 |
| 8,214,010 B2 * | 7/2012 | Courtney et al. | 600/407 |
| 2003/0103212 A1 | 6/2003 | Westphal et al. | |
| 2004/0051710 A1 * | 3/2004 | Hara | 345/419 |
| 2006/0039529 A1 * | 2/2006 | Tsubaki et al. | 378/41 |
| 2006/0039532 A1 * | 2/2006 | Wu et al. | 378/62 |
| 2006/0077395 A1 * | 4/2006 | Chan et al. | 356/497 |
| 2006/0122498 A1 * | 6/2006 | Sharpe | 600/425 |
| 2007/0019208 A1 * | 1/2007 | Toida et al. | 356/511 |
| 2007/0274435 A1 * | 11/2007 | Ning et al. | 378/4 |
| 2008/0025570 A1 * | 1/2008 | Fingler et al. | 382/107 |
| 2008/0234972 A1 * | 9/2008 | Tsukada et al. | 702/155 |
| 2010/0142780 A1 * | 6/2010 | Yasuno et al. | 382/131 |
| 2010/0194757 A1 * | 8/2010 | Tomidokoro et al. | 345/440 |
| 2011/0082335 A1 * | 4/2011 | Omori et al. | 600/109 |

OTHER PUBLICATIONS

Shinei Kudo, "Large Intestine Pit Pattern Diagnosis", Igaku-Shoin Ltd, ISBN 4-260-10673-2 YI2000, Jun. 1, 2005.

Srinivasan et al., "In vivo measurement of retinal physiology with high-speed ultrahigh-resolution optical coherence tomography", Optics Letters, vol. 31, No. 15, Aug. 1, 2006, pp. 2308-2310.

\* cited by examiner

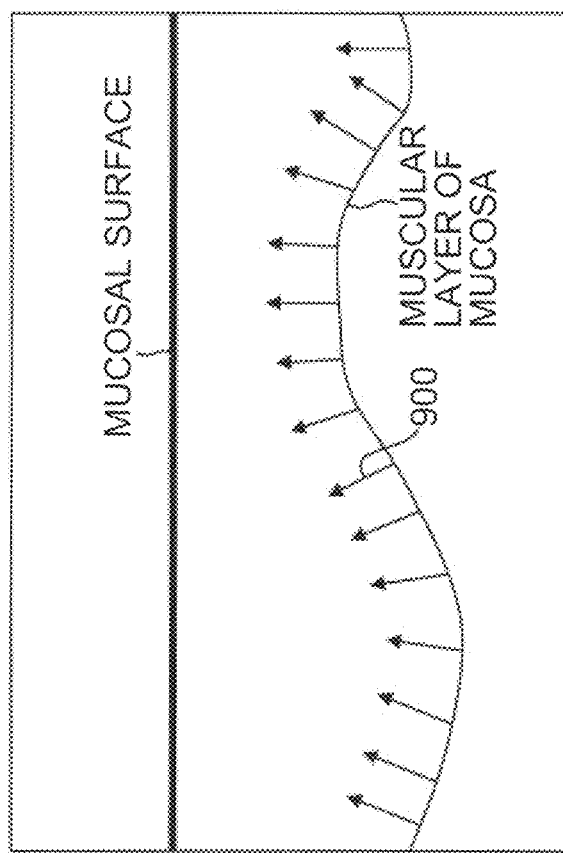

US 8,911,357 B2

OPTICAL STRUCTURE OBSERVATION APPARATUS AND STRUCTURE INFORMATION PROCESSING METHOD OF THE SAME

BACKGROUND OF THE INVENTION

1. Field of the Invention

The present invention relates to an optical structure observation apparatus and a structure information processing method of the same, and particularly relates to an optical structure observation apparatus characterized by display processing of structure information in a middle layer of a measured object having a layer structure and a structure information processing method of the same.

2. Description of the Related Art

In recent years, as one of the methods for non-invasively obtaining the tomographic images of the insides of living bodies in, for example, a medical field or the like, optical coherence tomography (OCT) measurement has come to be used. As compared with ultrasound measurement, the OCT measurement has the advantage that the resolution is about 10 μm and one digit higher, and the detailed tomographic images of the insides of living bodies can be obtained. Further, a plurality of images are acquired while the position is shifted in the direction vertical to a tomographic image, and a three-dimensional tomographic image can be obtained.

For example, a large intestine forms a layer structure of a mucosal layer, a muscular layer of mucosa, a submucosa, muscularis propria and the like as shown in FIG. 17, and as shown in FIG. 18, ducts (crypts) are formed to be regularly arranged substantially vertically in the mucosal layer with the muscular layer of mucosa as a basal plate ("Large Intestine Pit Pattern Diagnosis" written and edited by Shinei Kudo).

For example, in the endoscopic diagnosis of large intestine cancer, ducts (crypts) are observed under endoscope, and classification according to the mucosal structure of a large intestine called a pit pattern is performed. However, pit pattern diagnosis is only the method for determining the progress based on the image of a mucosal surface, and information relating to the depth of invasion is only empirical.

When a large intestine mucosa is measured three-dimensionally by the aforementioned OCT measurement, the three-dimensional structure of a duct structure can be extracted, and as the information of the region near the surface, the structure similar to the pit pattern can be obtained. Further, since the three-dimensional structure can be obtained in the OCT measurement, change in the depth direction of the duct structure is observed.

It is known that the duct structure of a mucosal layer crumbles when cancer is caused in a large intestine ("Large Intestine Pit Pattern Diagnosis" written and edited by Shinei Kudo). More specifically, normal crypt forms the shape (normal state) as type I of FIG. 18, but it is known that due to canceration, the shape of a crypt deforms as in FIG. 19, for example, and the crypt itself finally crumbles as shown in FIG. 20 (lesion state).

Meanwhile, it is known that by three-dimensionally reconstructing a tomographic image by OCT measurement, extracting the crypt from the tomographic image, and analyzing the shape, difference between a normal part and a lesion part can be numerically analyzed (Journal of Biomedical Optics Vol. 13, p. 054055 (2008)). However, with extraction of the crypt, the structure is not visually understandable, and it is difficult to image a change in the stereoscopic lesion part.

Further, an art is disclosed, in which the surface of a measured object of a three-dimensional structure is extracted and made planar, and the structure information is imaged as a change in the depth direction (Japanese Patent Application Laid-Open No. 2007-225349).

However, for example, in the case of a large intestine, to what degree the lesion part approaches the muscular layer of mucosa, and whether invasion to the muscular layer of mucosa is present or not are important for cancer diagnosis. However, if a mucosal surface is made planar by using the art of Japanese Patent Application Laid-Open No. 2007-225349, ducts (crypts) are formed substantially vertical in the mucosal layer with the muscular layer of mucosa as a basal plate in the optical structure information as shown in FIG. 21, and therefore, the orientations (arrows 900 in FIG. 21) of the ducts (crypts) become random orientations, and there is the problem that visual judgment of the state of the ducts (crypts) (normal state of FIG. 18, or the lesion states of FIGS. 19 and 20) becomes difficult.

SUMMARY OF THE INVENTION

The present invention is made in view of such circumstances, and has an object to provide an optical structure observation apparatus which can visually determine structure information with a middle layer in a measured object having a layer structure as a basal plate, and a structure information processing method of the same.

In order to attain the above-described object, an optical structure observation apparatus of a first aspect of the present invention is an optical structure observation apparatus which acquires a plurality of pieces of optical structure information of a measured object obtained by scanning a scan surface constituted of a first direction which is a depth direction of the measured object having a layer structure and a second direction orthogonal to the first direction, by using a low coherence light, while shifting a position along a third direction which is a direction orthogonal to the scan surface, and constructs an optical stereoscopic structure image based on a plurality of pieces of the optical structure information which are acquired, and is configured by including a middle layer extracting device which extracts a desired middle layer in the measured object from the optical structure information configuring the optical stereoscopic structure image, a layer flattening device which performs flattening to make the middle layer a plane at a same depth position, a structure image converting device which reconstructs the optical stereoscopic structure image with the flattened middle layer as a reference layer, and generates a three-dimensional converted optical structure image, and a display control device which images at least the three-dimensional converted optical structure image, and causes a display device to display the image.

In the optical structure observation apparatus according to the first aspect, the optical stereoscopic structure image is reconstructed with the flattened middle layer as the reference layer, the three-dimensional converted optical structure image is generated, and at least the three-dimensional converted optical structure image is imaged and displayed on the display device, whereby the structure information with the middle layer in the measured object having a layer structure as a basal plate can be visually determined.

The optical structure observation apparatus according to a second aspect of the present invention which is the optical structure observation apparatus according to the first aspect can be configured by further including an extracted region setting device which sets an extracted region with a parallel surface located at a desired height parallel with the reference layer as a parallel section, on the three-dimensional converted optical structure image, a region information extracting device which extracts the optical structure information in the extracted region, and a parallel sectional image generating device which generates a parallel sectional image based on the optical structure information in the extracted region extracted by the region information extracting device.

In the optical structure observation apparatus according to a third aspect of the present invention, in the optical structure observation apparatus according to the second aspect, the region information extracting device can set a plurality of extracted regions constituted of different regions having a plurality of parallel surfaces located at a plurality of desired heights parallel with the reference layer as respective parallel sections, and the parallel sectional image generating device can generate a plurality of the parallel sectional images for each of the plurality of extracted regions.

In the optical structure observation apparatus according to a fourth aspect of the present invention, in the optical structure observation apparatus according to the second or the third aspect, the display control device can cause the display device to display the parallel sectional image.

In the optical structure observation apparatus according to a fifth aspect of the present invention, the optical structure observation apparatus according to the third aspect can be configured by further including an image synthesizing device which generates a synthesized image with a plurality of the parallel sectional images being synthesized.

In the optical structure observation apparatus according to a sixth aspect of the present invention, in the optical structure observation apparatus according to the fifth aspect, the display control device can cause the display device to display the synthesized image.

In the optical structure observation apparatus according to a seventh aspect of the present invention, in the optical structure observation apparatus according to any one of the second to the sixth aspects, the parallel sectional image generating device can generate a parallel sectional image by performing any one processing of integration processing, maximum intensity projection, and minimum intensity projection for the optical structure information in the extracted region along a direction orthogonal to the reference layer.

In the optical structure observation apparatus according to an eighth aspect of the present invention, in the optical structure observation apparatus according to any one of the second to seventh aspects, the parallel sectional image is preferably of a crypt structure or an arrangement pattern of a blood vessel.

In the optical structure observation apparatus according to a ninth aspect of the present invention, in the optical structure observation apparatus according to any one of the first to eighth aspects, the middle layer is preferably a muscular layer of mucosa or a basal layer.

A structure information processing method of an optical structure observation apparatus according to a tenth aspect of the present invention is a structure information processing method of an optical structure observation apparatus which acquires a plurality of pieces of optical structure information of a measured object obtained by scanning a scan surface constituted of a first direction which is a depth direction of the measured object having a layer structure and a second direction orthogonal to the first direction, by using a low coherence light, while shifting a position in a third direction which is a direction orthogonal to the scan surface, and constructs an optical stereoscopic structure image based on a plurality of pieces of the optical structure information which are acquired, and can be configured by including a middle layer extracting step of extracting a desired middle layer in the measured object from the optical structure information configuring the optical stereoscopic structure image, a layer flattening step of flattening the middle layer, a structure image converting step of reconstructing the optical stereoscopic structure image with the flattened middle layer as a reference layer, and generating a three-dimensional converted optical structure image, and a display control step of imaging at least the three-dimensional converted optical structure image, and causing a display device to display the image.

In the structure information processing method of an optical structure observation apparatus according to the tenth aspect, the optical stereoscopic structure image is reconstructed with the flattened middle layer as the reference layer, the three-dimensional converted optical structure image is generated, and at least the three-dimensional converted optical structure image is imaged and displayed on the display device, whereby the structure information with the middle layer in the measured object having a layer structure as a basal plate can be visually determined.

The structure information processing method of an optical structure observation apparatus according to an eleventh aspect of the present invention which is the structure information processing method of an optical structure observation apparatus according to the tenth aspect can be configured by further including an extracted region setting step of setting an extracted region with a parallel surface located at a desired height parallel with the reference layer as a parallel section, on the three-dimensional converted optical structure image, a region information extracting step of extracting the optical structure information in the extracted region, and a parallel sectional image generating step of generating a parallel sectional image based on the optical structure information in the extracted region extracted in the region information extracting step.

In the structure information processing method of an optical structure observation apparatus according to a twelfth aspect of the present invention, in the structure information processing method of an optical structure observation apparatus according to the eleventh aspect, the region information extracting step can set a plurality of extracted regions constituted of different regions having a plurality of parallel surfaces located at a plurality of desired heights parallel with the reference layer as parallel sections respectively, and the parallel sectional image generating step can generate a plurality of the parallel sectional images for each of the plurality of extracted regions.

In the structure information processing method of an optical structure observation apparatus according to a thirteenth aspect of the present invention, in the structure information processing method of an optical structure observation apparatus according to the eleventh or the twelfth aspect, the display control step can cause the display device to display the parallel sectional image.

In the structure information processing method of an optical structure observation apparatus according to a fourteenth aspect of the present invention, the structure information processing method of an optical structure observation apparatus according to the twelfth aspect can be configured by further including an image synthesizing step of generating a synthesized image with a plurality of the parallel sectional images being synthesized.

In the structure information processing method of the optical structure observation apparatus according to the fifteenth aspect of the present invention, in the structure information processing method of an optical structure observation apparatus according to the fourteenth aspect, the display control step can cause the display device to display the synthesized image.

In the structure information processing method of an optical structure observation apparatus according to a sixteenth aspect of the present invention, in the structure information processing method of an optical structure observation apparatus according to any one of the eleventh to fifteenth aspects, the parallel sectional image generating step can generate a parallel sectional image by performing any one processing of integration processing, maximum intensity projection, and minimum intensity projection for the optical structure information in the extracted region along a direction orthogonal to the reference layer.

In the structure information processing method of an optical structure observation apparatus according to a seventeenth aspect of the present invention, in the structure information processing method of an optical structure observation apparatus according to any one of the eleventh to sixteenth aspects, the parallel sectional image is preferably of a crypt structure or an arrangement pattern of a blood vessel.

In the structure information processing method of an optical structure observation apparatus according to an eighteenth aspect of the present invention, in the structure information processing method of an optical structure observation apparatus according to any one of the tenth to seventeenth aspects, the middle layer is preferably a muscular layer of mucosa or a basal layer.

As described above, according to the present invention, there is provided the effect of being capable of visually determining structure information with the middle layer in the measured object having a layer structure as the basal plate.

BRIEF DESCRIPTION OF THE DRAWINGS

FIG. 21 is a view showing a state of ducts in optical structure information in which a mucosal surface is made planar.

DETAILED DESCRIPTION OF THE PREFERRED EMBODIMENTS

Hereinafter, a best mode for carrying out the present invention will be described.

<Appearance of Diagnostic Imaging Apparatus>

Figure 1:
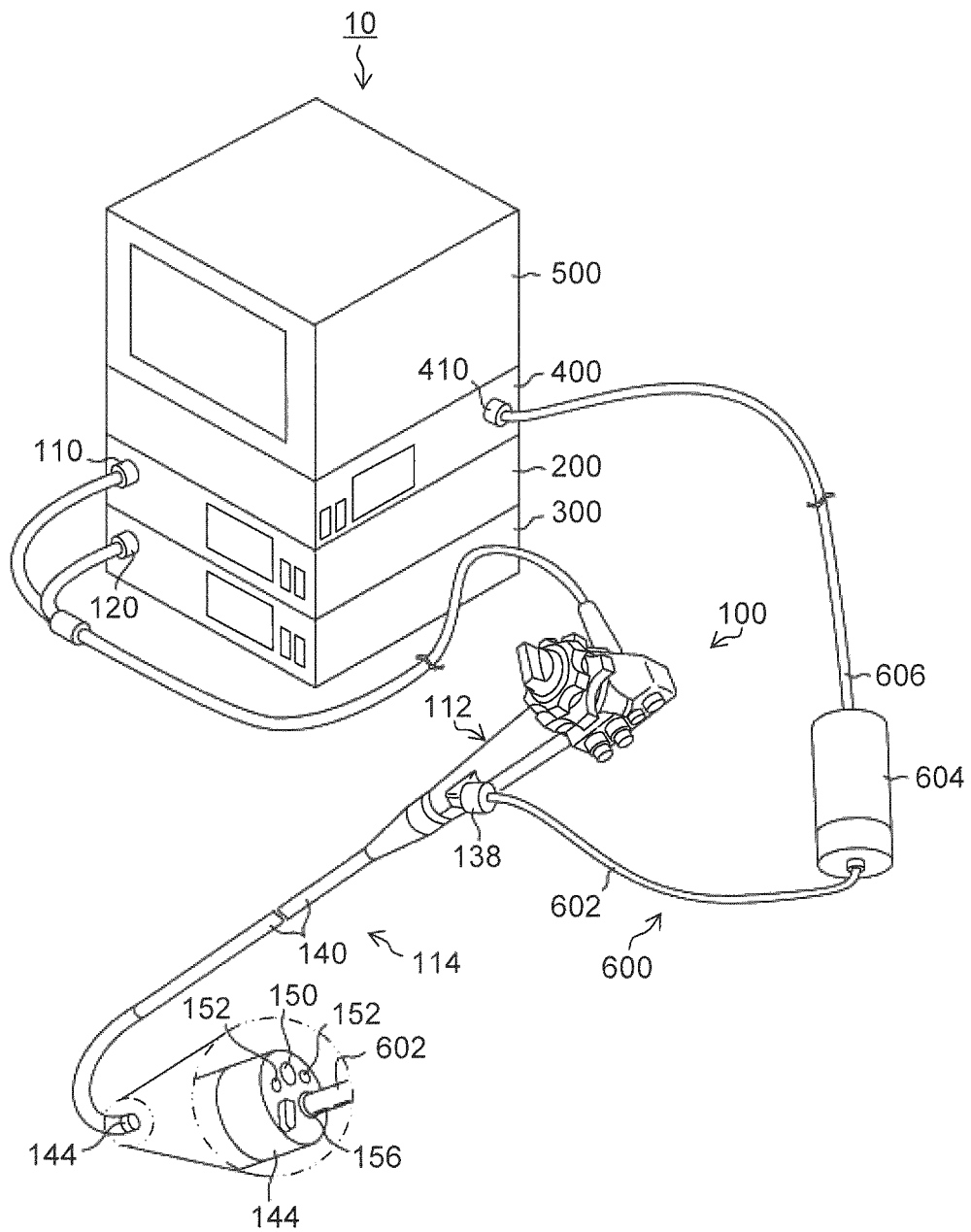
FIG. 1 is an outside view showing a diagnostic imaging apparatus according to the present invention.

FIG. 1 is an outside view showing a diagnostic imaging apparatus according to the present invention.

As shown in FIG. 1, a diagnostic imaging apparatus 10 as an optical structure observation apparatus of the present embodiment is mainly configured by an endoscope 100, an endoscope processor 200, a light source device 300, an OCT processor 400 and a monitor device 500. The endoscope processor 200 may be configured to contain the light source device 300.

The endoscope 100 includes a hand operation section 112, and an insertion section 114 provided to connect to the hand operation section 112. An operator grips the hand operation section 112 and operates the hand operation section 112, inserts the insertion section 114 into a body of a subject, and thereby performs observation.

The hand operation section 112 is provided with a forceps insertion section 138, and the forceps insertion section 138 is caused to communicate with a forceps port 156 of a tip end portion 144. In the diagnostic imaging apparatus 10 according to the present invention, by inserting an OCT probe 600 from the forceps insertion section 138, the OCT probe 600 is guided out from the forceps port 156. The OCT probe 600 is configured by an insertion section 602 which is inserted from the forceps insertion section 138 and is guided out from the forceps port 156, an operation section 604 for an operator to operate the OCT probe 600, and a cable 606 which is connected to the OCT processor 400 via a connector 410.

<Configuration of Endoscope, Endoscope Processor and Light Source Device>

[Endoscope]

An observation optical system 150, an illumination optical system 152 and a CCD (not illustrated) are placed at the tip end portion 144 of the endoscope 100.

The observation optical system 150 forms an image of a subject on a light receiving surface of the CCD not illustrated, and the CCD converts the subject image formed on the light receiving surface into an electrical signals by each light receiving elements. The CCD of this embodiment is a color CCD in which color filters of three primary colors of red (R), green (G) and blue (B) are placed in predetermined arrangement (Bayer arrangement, honeycomb arrangement) in the light receiving elements constituting pixels.

[Light Source Device]

The light source device 300 causes visible light to be incident on a light guide not illustrated. One end of the light guide is connected to the light source device 300 via an LG connector 120, and the other end of the light guide is opposed to the illumination optical system 152. The light emitted from the light source device 300 is emitted from the illumination optical system 152 via the light guide and illuminates the visual field range of the observation optical system 150.

[Endoscope Processor]

To the endoscope processor 200, an image signal outputted from the CCD is inputted through an electric connector 110. The analog image signal is converted into a digital image signal in the endoscope processor 200, and is subjected to processing necessary for being displayed on the screen of the monitor device 500.

The data of the observation image obtained in the endoscope 100 is outputted to the endoscope processor 200, and the image is displayed on the monitor device 500 which is connected to the endoscope processor 200.

<Internal Configurations of OCT Processor and OCT Probe>

Figure 2:
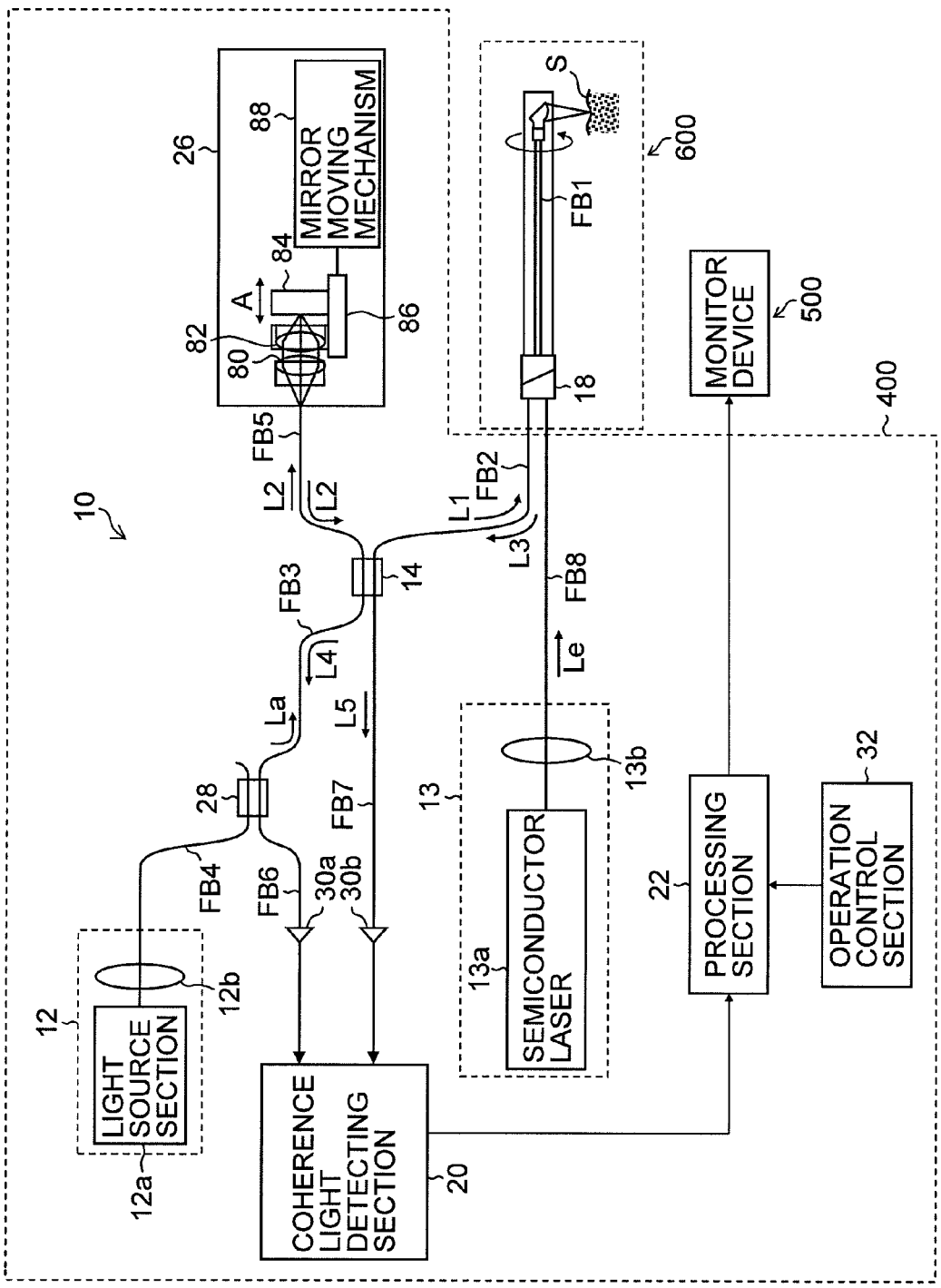
FIG. 2 is a block diagram showing an internal configuration of an OCT processor of FIG. 1.

FIG. 2 is a block diagram showing the internal configuration of the OCT processor of FIG. 1.

[OCT Processor]

The OCT processor 400 and the OCT probe 600 shown in FIG. 2 are for acquiring the optical tomographic image of a measured object by an optical coherence tomography (OCT: Optical Coherence Tomography) measurement method, and have a first light source (first light source unit) 12 which emits a light La for measurement, an optical fiber coupler (branching/multiplexing section) 14 which branches the light La emitted from the first light source 12 into a measuring light (first luminous flux) L1 and a reference light L2, and generates a coherence light L4 by multiplexing a return light L3 from a measurement object S which is a subject and the reference light L2, the OCT probe 600 including a rotation side optical fiber FB1 which guides the measuring light L1 branched with the optical fiber coupler 14 to the measurement subject, and guides the return light L3 from the measurement object, a fixed side optical fiber FB2 which guides the measuring light L1 to the rotation side optical fiber FB1 and guides the return light L3 guided by the rotation side optical fiber FB1, an optical connector 18 which connects the rotation side optical fiber FB1 rotatably with respect to the fixed side optical fiber FB2, and transmits the measuring light L1 and the return light L3, a coherence light detecting section 20 which detects the coherence light L4 generated in the optical fiber coupler 14 as a coherence signal, and a processing section 22 which processes the coherence signal detected by the coherence light detecting section 20 to acquire optical structure information. Further, an image is displayed on the monitor device 500 based on the optical structure information acquired in the processing section 22.

Further, the OCT processor 400 has a second light source (second light source unit) 13 which emits an aiming light (second luminous flux) Le for indicating a mark of measurement, an optical path length adjusting section 26 which adjusts an optical path length of the reference light L2, an optical fiber coupler 28 which disperses the light La which is emitted from the first light source 12, detectors 30a and 30b which detect return lights L4 and L5 which are multiplexed in the optical fiber coupler 14, and an operation control section 32 which inputs various conditions to the processing section 22, and makes change of setting and the like.

In the OCT processor 400 shown in FIG. 2, as the optical paths for guiding and transmitting various lights including the aforementioned emission light La, aiming light Le, measuring light L1, reference light L2, return light L3 and the like to and from the components such as each of optical devices, various optical fibers FR (FB3, FB4, FB5, FB6, FB7, FB8 and the like) including the rotation side optical fiber FB1 and the fixed side optical fiber FB2 are used.

The first light source 12 emits light (for example, laser light or low coherence light of a wavelength of 1.3 μm) for measurement of OCT, and includes a light source section 12a which emits laser light or low coherence light La, and a lens 12b which gathers the light La emitted from the light source section 12a. Though described in detail later, the light La emitted from the first light source 12 is divided into the measuring light L1 and the reference light L2 in the optical fiber coupler 14 through the optical fibers FB4 and FB3, and the measuring light L1 is inputted into the optical connector 18.

Further, the second light source 13 emits a visible light in order to make the measurement region easily conformable as the aiming light Le. For example, a red semiconductor laser light of a wavelength of 0.66 μm, an He—Ne laser light of a wavelength of 0.63 μm, a blue semiconductor laser light of a wavelength of 0.405 μm and the like can be used. Thus, as the second light source 13, a semiconductor laser 13a which emits a laser light of, for example, red, blue or green, and a lens 13b which gathers the aiming light Le emitted from the semiconductor laser 13a. The aiming light Le which is emitted from the second light source 13 is inputted to the optical connector 18 through the optical fiber FB8.

In the optical connector 18, the measuring light L1 and the aiming light Le are multiplexed, and are guided to the rotation side optical fiber FB1 in the OCT probe 600.

The optical fiber coupler (branching/multiplexing section) 14 is configured by an optical fiber coupler of, for example, 2 by 2, and is optically connected to the fixed side optical fiber FB2, the optical fiber FB3 the optical fiber FB5 and the optical fiber FB7, respectively.

The optical fiber coupler 14 divides the light La which is incident from the first light source 12 through the optical fibers FB4 and FB3 into the measuring light (first luminous flux) L1 and the reference light L2, causes the measuring light L1 to be incident on the fixed side optical fiber FB2, and causes the reference light L2 to be incident on the optical fiber FB5.

Further, the optical fiber coupler 14 multiplexes the light L2 which is incident on the optical fiber F85, is subjected to change of the frequency shift and optical path length by the optical path length adjusting section 26 which will be described later, and returns through the optical fiber FB35, and the light L3 which is acquired by the OCT probe 600 which will be described later and is guided from the fixed side optical fiber FB2, and emits the multiplexed light to the optical fiber FB3 (FB6) and the optical fiber FB7.

The OCT probe 600 is connected to the fixed side optical fiber FB2 via the optical connector 18, and the measuring light L1, which is multiplexed with the aiming light Le, is incident on the rotation side optical fiber FB1 from the fixed side optical fiber FB2 through the optical connector 18. The incident measuring light L1 multiplexed with the aiming light Le is transmitted by the rotation side optical fiber FB1 to be irradiated to the measurement object S. The return light L3 from the measurement object S is acquired, the acquired return light L3 is transmitted by the rotation side optical fiber FB1, and is emitted to the fixed side optical fiber FB2 through the optical connector 18.

The optical connector 18 multiplexes the measuring light (first luminous flux) L1 and the aiming light (second luminous flex) Le.

The coherence light detecting section 20 is connected to the optical fiber FB6 and the optical fiber FB7, and detects the coherence lights L4 and L5 which are generated by multiplexing the reference light L2 and the return light L3 by the optical fiber coupler 14 as coherence signals.

Here, the OCT processor 400 has the detector 30a which is provided on the optical fiber FB6 branched from the optical fiber coupler 28 and detects the light intensity of the laser light L4, and the detector 30b which detects the light intensity of the coherence light L5 on the optical path of the optical fiber FB7.

The coherence light detecting section 20 extracts only coherence amplitude components from the coherence light L4 detected from the optical fiber FB6 and the coherence light L5 detected from the optical fiber FB7 based on the detection result of the detector 30a and the detector 30b.

The processing section 22 detects the region where the OCT probe 600 and the measurement object S are in contact in the measurement position, more accurately, the region where the surface of the probe outer barrel (which will be described later) of the OCT probe 600 and the surface of the measurement object S are regarded to be in contact with each other from the coherence signal extracted in the coherence light detecting section 20, further acquires the optical structure information from the coherence signal detected in the coherence light detecting section 20, generates the optical stereoscopic structure image based on the acquired optical structure information, and outputs the image produced by applying various processing to the optical stereoscopic structure image to the monitor device 500. The detailed configuration of the processing section 22 will be described later.

The optical path length adjusting section 26 is disposed at the emission side (more specifically, the end portion of the optical fiber FB5 at the side opposite from the optical fiber coupler 14) of the reference light L2, of the optical fiber FB5.

The optical path length adjusting section 26 has a first optical lens 80 which makes the light emitted from the optical fiber FB5 a parallel light, a second optical lens 82 which gathers the light made a parallel light by the first optical lens 80, a reflective mirror 84 which reflects the light gathered by the second optical lens 82, a base 86 which supports the second optical lens 82 and the reflective mirror 84, and a mirror moving mechanism 88 which moves the base 86 in the direction parallel with the optical axis direction A, and adjusts the optical path length of the reference light L2 by changing the distance between the first optical lens 80 and the second optical lens 82.

The first optical lens 80 makes the reference light L2 emitted from the core of the optical fiber FB5 a parallel light, and gathers the reference light L2 reflected by the reflective mirror 84 at the core of the optical fiber FB5.

Further, the second optical lens 82 gathers the reference light L2 which is made a parallel light by the first optical lens 80 on the reflective mirror 84, and makes the reference light L2 reflected by the reflective mirror 84 a parallel light. In this manner, a confocal optical system is formed by the first optical lens 80 and the second optical lens 82.

Further, the reflective mirror 84 is disposed at the focal point of the light gathered by the second optical lens 82, and reflects the reference light L2 gathered by the second optical lens 82.

Thereby, the reference light L2 which is emitted from the optical fiber FB5 is made a parallel light by the first optical lens 80, and is gathered on the reflective mirror 84 by the second optical lens 82. Thereafter, the reference light L2 reflected by the reflective mirror 84 is made a parallel light by the second optical lens 82, and is gathered at the core of the optical fiber FB5 by the first optical lens 80.

Further, the base 86 fixes the second optical lens 82 and the reflective mirror 84, and the mirror moving mechanism 88 moves the base 86 in the direction of the optical axis of the first optical lens 80 (direction of arrows A in FIG. 2).

By moving the base 86 in the direction of arrows A with the mirror moving mechanism 88, the distance between the first optical lens 80 and the second optical lens 82 can be changed, and the optical path length of the reference light L2 can be adjusted.

The operation control section 32 as an extracted region setting device has an input device such as a keyboard and a mouse, and a control device which manages various conditions based on the inputted information, and is connected to the processing section 22. The operation control section 32 performs input, setting, change and the like of various processing conditions and the like in the processing section 22 based on the instruction of the operator which is inputted from the input device.

The operation control section 32 may cause the monitor device 500 to display an operation screen, or may be additionally provided with a display section and causes the display section to display the operation screen. Further, in the operation control section 32, the operation control of the first light source 12, the second light source 13, the optical connector 18, the coherence light detecting section 20, the optical path length and the detectors 30a and 30b and setting of various conditions may be performed.

[OCT Probe]

Figure 3:
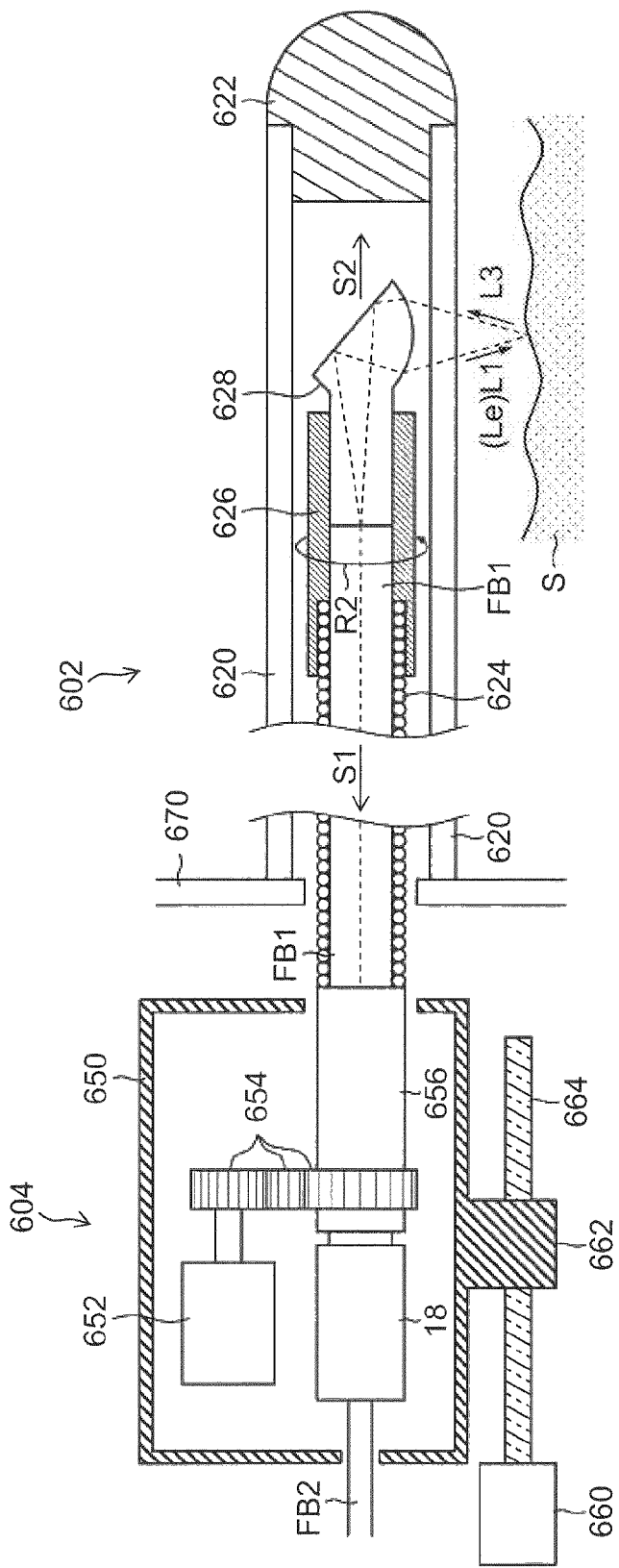
FIG. 3 is a sectional view of an OCT probe of FIG. 2.

FIG. 3 is a sectional view of the OCT probe of FIG. 2.

As shown in FIG. 3, a tip end portion of the insertion section 602 has a probe outer barrel 620, a cap 622, the rotation side optical fiber FB1, a spring 624, a fixing member 626 and an optical lens 628.

The probe outer barrel (sheath) 620 is a cylindrical member having flexibility, and is made of a material through which the measuring light L1 multiplexed with the aiming light Le in the optical connector 18 and the return light L3 transmit. In the probe outer barrel 620, a part of the tip end (tip end of the rotation side optical fiber FB1 at the side opposite from the optical connector 18, hereinafter, called the tip end of the probe outer barrel 620) side where the measuring light L1 (aiming light Le) and the return light L3 pass only has to be formed of a material (transparent material) which transmits the light over the entire periphery, and the portions other than the tip end may be formed of a material which does not transmit a light.

The cap 622 is provided at the tip end of the probe outer barrel 620, and closes the tip end of the probe outer barrel 620.

The rotation side optical fiber FB1 is a linear member, housed in the probe outer barrel 620 along the probe outer barrel 620, guides the measuring light L1, which is emitted from the fixed side optical fiber FB2 and is multiplexed with the aiming light Le emitted from the optical fiber FB8 in the optical connector 18, to the optical lens 628, guides the return light L3 from the measurement object S, which is acquired with the optical lens 628 after the measuring light L1 (aiming light Le) is irradiated to the measurement object S to the optical connector 18, and causes the return light L3 to be incident on the fixed side optical fiber FB2.

Here, the rotation side optical fiber FB1 and the fixed side optical fiber FB2 are connected by the optical connector 18, and are optically connected in the state in which rotation of the rotation side optical fiber FB1 is not transmitted to the fixed side optical fiber FB2. Further, the rotation side optical fiber FB1 is disposed in the state rotatable with respect to the probe outer barrel 620 and movable in the axial direction of the probe outer barrel 620.

The spring 624 is fixed to the outer periphery of the rotation side optical fiber FB1. Further, the rotation side optical fiber FB1 and the spring 624 are connected to the optical connector 18.

The optical lens 628 is disposed at the tip end (tip end of the rotation side optical fiber FB1 at the side opposite from the optical connector 18) at the measuring side of the rotation side optical fiber FB1, and the tip end portion is formed into a substantially spherical shape for gathering the measuring light L1 (aiming light Le) emitted from the rotation side optical fiber FB1 onto the measurement object S.

The optical lens 628 irradiates the measurement object S with the measuring light L1 (aiming light Le) emitted from the rotation side optical fiber FB1, gathers the return light L3 from the measurement object S, and causes the return light L3 to be incident on the rotation side optical fiber FB1.

The fixing member 626 is disposed on the outer peripheries of the connecting portions of the rotation side optical fiber FB1 and the optical lens 628, and fixes the optical lens 628 to the end portion of the rotation side optical fiber FB1. Here, the fixing method of the rotation side optical fiber FB1 and the optical lens 628 by the fixing member 626 is not especially limited, and the fixing member 626, and the rotation side optical fiber FB1 and the optical lens 628 may be bonded and fixed by an adhesive, or may be fixed with a mechanical structure using a bolt or the like. As the fixing member 626, any member such as a zirconia ferrule and a metal ferrule may be used as long as it is used for fixing, holding or protecting the optical fiber.

Further, the rotation side optical fiber FB1 and the spring 624 are connected to a rotary barrel 656 which will be described later, and by rotating the rotation side optical fiber FB1 and the spring 624 by the rotary barrel 656, the optical lens 628 is rotated in the direction of the arrow R2 with respect to the probe outer barrel 620. Further, the optical connector 18 includes a rotary encoder, and detects the irradiating position of the measuring light L1 from the positional information (angle information) of the optical lens 628 based on the signal from the rotary encoder. More specifically, the optical connector 18 detects the angle with respect to the reference position in the rotational direction of the rotating optical lens 628, and detects the measuring position.

Further, the rotation side optical fiber FB1, the spring 624, the fixing member 626 and the optical lens 628 are configured to be movable in the direction of the arrow S1 (forceps port direction) and the direction of S2 (direction of the tip end of the probe outer barrel 620) inside the probe outer barrel 620 by a drive section which will be described later.

Further, the left side of FIG. 3 is a view showing the outline of the drive section for the rotation side optical fiber FB1 and the like in the operation section 604 of the OCT probe 600.

The probe outer barrel 620 is fixed to a fixing member 670. In contrast with this, the rotation side optical fiber FB1 and the spring 624 are connected to the rotary barrel 656, and the rotary barrel 656 is configured to rotate through a gear 654 in accordance with the rotation of a motor 652. The rotary barrel 656 is connected to the optical connector 18, and the measuring light L1 and the return light L3 are transmitted between the rotation side optical fiber FB1 and the fixed side optical fiber FB2 through the optical connector 18.

Further, a frame 650 containing them includes a support member 662, and the support member 662 has a screw hole not illustrated. A ball screw 664 for advance and retreat movement is engaged in the screw hole, and a motor 660 is connected to the ball screw 664 for advance and retreat movement. Accordingly, by rotationally driving the motor 660, the frame 650 is moved to advance and retreat, and thereby, the rotation side optical fiber FB1, the spring 624, the fixing member 626, and the optical lens 628 can be moved in the directions of S1 and S2 in FIG. 3.

The OCT probe 600 is configured as above, and the rotation side optical fiber FB1 and the spring 624 are rotated in the direction of the arrow R2 in FIG. 3 by the optical connector 18, whereby the OCT probe 600 irradiates the measurement object S with the measuring light L1 (aiming light Le) emitted from the optical lens 623 while scanning in the direction of the arrow R2 (the circumferential direction of the probe outer barrel 620), and acquires the return light L3. The aiming light Le is irradiated to the measurement object S as a spot light of, for example, a blue color, red color or green color, and the reflection light of the aiming light Le is displayed on the observation image displayed on the monitor device 500 as a bright spot.

Thereby, in the entire periphery in the circumferential direction of the probe outer barrel 620, a desired region of the measurement object S can be accurately captured, and the return light L3 reflected at the measurement object S can be acquired.

Further, when a plurality of pieces of optical structure information for generating an optical stereoscopic structure image is to be acquired, the optical lens 628 is moved to the terminal end of the movable range in the direction of the arrow S1 by the drive section, moves in the direction of S2 by a predetermined amount while acquiring the optical structure information constituted of a tomographic image, or moves to the terminal end in the movable range while alternately repeating optical structure information acquisition and movement by a predetermined amount in the direction of S2.

Like this, a plurality of pieces of optical structure information in a desired range are obtained for the measurement object S, and based on a plurality of pieces of optical structure information, an optical stereoscopic structure image can be obtained.

More specifically, the optical structure information in the depth direction (first direction) of the measurement object S is obtained by the coherence signal, and scanning is performed in the direction of the arrow R2 (circumferential direction of the probe outer barrel 620) of FIG. 3 for the measurement object S, whereby, the optical structure information on the scan surface constituted of the first direction and the second direction orthogonal to the first direction can be acquired, and by further moving the scan surface along the third direction orthogonal to the scan surface, a plurality of pieces of optical structure information for generating the optical stereoscopic structure image can be acquired.

Figure 4:
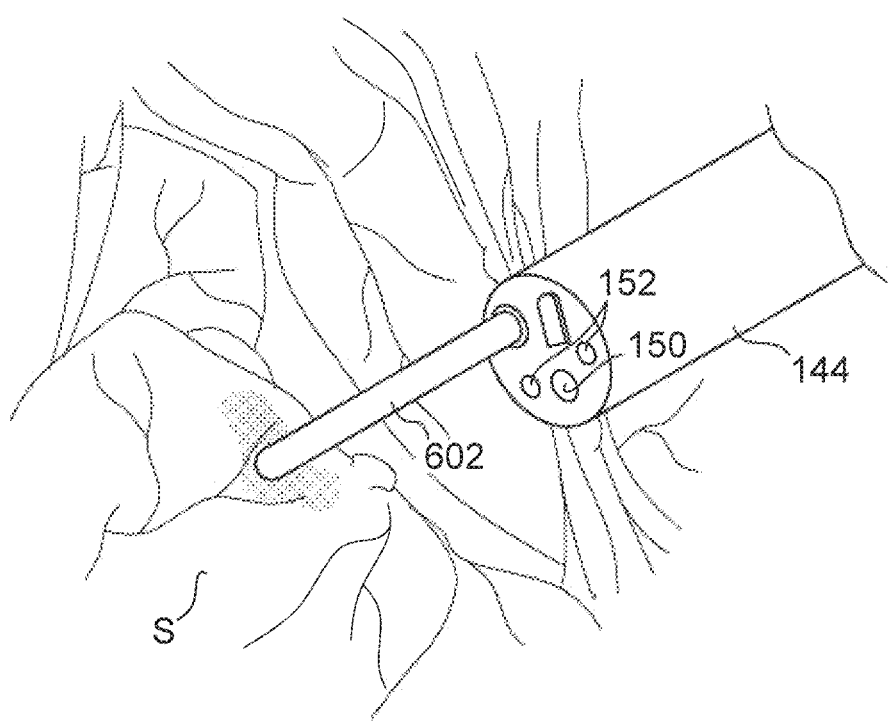
FIG. 4 is a view showing a state of obtaining optical structure information by using the OCT probe guided out from a forceps port of an endoscope of FIG. 1.

FIG. 4 is a view showing the state in which optical structure information is obtained by using the OCT probe 600 guided out of the forceps port 156 of the endoscope 100 of FIG. 1. As shown in FIG. 4, the tip end portion 144 of the insertion section 602 of the OCT probe 600 is moved close to a desired region of the measurement object S, and optical structure information is obtained. When a plurality of pieces of optical structure information in a desired range is to be acquired, the OCT probe 600 main body does not have to be moved, but the optical lens 628 only has to be moved in the probe outer barrel 620 by the aforementioned drive section.

[Processing Section]

Figure 5:
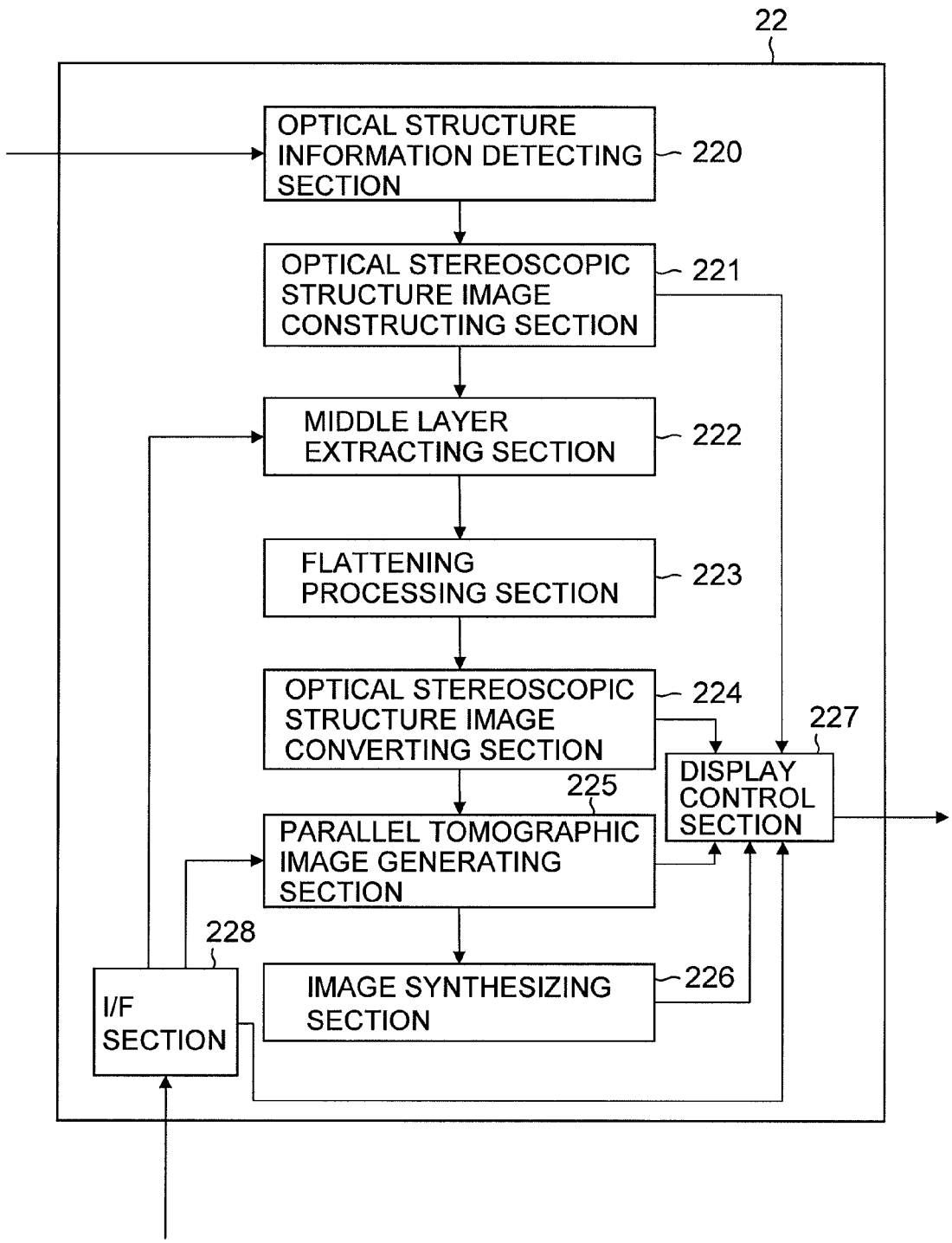
FIG. 5 is a block diagram showing a configuration of a processing section of FIG. 2.

FIG. 5 is a block diagram showing a configuration of the processing section of FIG. 2.

As shown in FIG. 5, the processing section 22 of the OCT processor 400 is configured by including an optical structure information detecting section 220, an optical stereoscopic structure image constructing section 221, a middle layer extracting section 222 as a middle layer extracting device, a flattening processing section 223 as a layer flattening device, an optical stereoscopic structure image converting section 224 as a structure image converting device, a parallel tomographic image generating section 225 as a region information extracting device and a parallel sectional image generating device, an image synthesizing section 226 as an image synthesizing device, a display control section 227 as a display control device and an I/F section 228.

The optical structure information detecting section 220 detects optical structure information from the coherence signal detected in the coherence light detecting section 20. Further, the optical stereoscopic structure image constructing section 221 generates an optical stereoscopic structure image based on the optical structure information detected by the optical structure information detecting section 220.

The middle layer extracting section 222 extracts a muscular layer of mucosa as a middle layer when the measurement object S is the mucosa of a large intestine, for example. When the mucosal epithelium is an original squamous epithelium as in an esophagus, the middle layer extracting section 222 extracts a basal membrane (basal layer) as a middle layer.

The middle layer can be set by a setting signal of the operation control section 32 via the I/F section 228. The flattening processing section 223 shifts the data in the depth direction so that the extracted muscular layer of mucosa is in a certain reference position in order to flatten the layer position of the muscular layer of mucosa extracted by the middle layer extracting section 222. The flattening processing section 223 may be configured so as to perform flattening processing by fitting the position of the muscular layer of mucosa to a certain optical function from the two-dimensional optical structure information or the three-dimensional optical structure information.

The optical stereoscopic structure image converting section 224 converts an optical stereoscopic structure image so that a muscular layer of mucosa becomes the reference surface of the optical stereoscopic structure image.

The reference surface is not limited to a muscular layer of mucosa, and may be a mucosal surface, a basal layer (when the mucosal epithelium is an original squamous epithelium), but in the case of a large intestine, the muscular layer of mucosa is more desirably set as the reference surface.

The parallel tomographic image generating section 225 integrates the optical structure information of the extracted region along the direction orthogonal to the reference layer in a certain fixed range at an optional height from a muscular layer of mucosa which is set based on the setting signal of the operation control section 32 via the I/F section 228 in the optical structure information on the scan surface configuring the optical stereoscopic structure image converted by the optical stereoscopic structure image converting section 224, for example, and generates a parallel sectional image which is an integrated image in which a pit pattern appears.

The parallel tomographic image generated by the parallel tomographic image generating section 225 is not limited to an integrated image, but may be any one of an MIP (Maximum intensity projection) image and an MINIP (Minimum intensity projection) image. The processing method can be set by the setting signal of the operation control section 32 via the I/F section 223, and the processing method is desirably used properly so that the characteristics of the structure can be seen by being highlighted. Further, in the structure of regular arrangement such as a duct structure of a large intestine normal region, an integrated image is preferable.

Further, the parallel tomographic image generated by the parallel tomographic image generating section 225 may be a sectional image of an extracted region without performing processing such as integration processing, maximum intensity projection and minimum intensity projection.

The image synthesizing section 226 synthesizes a plurality of parallel sectional images generated by the parallel tomographic image generating section 225, which correspond to a plurality of extracted regions, when a plurality of extracted regions are set by the setting signal of the operation control section 32 via the I/F section 228, and generates, for example, a synthesized image in which two parallel sectional images are arranged in parallel to be developed on one screen, or a synthesized image in which one of two parallel sectional images is superimposed on the other.

The display control section 227 outputs the image of the optical stereoscopic structure image from the optical stereoscopic structure image constructing section 221 and the optical structure information on the scan surface, the image of the optical stereoscopic structure image from the optical stereoscopic structure image converting section 224 and the optical structure image information on the scan surface, the parallel sectional image from the parallel tomographic image generating section 225, and the synthesized image from the image synthesizing section 226 to the monitor device 500 selectively by the instruction signal of the operation control section 32 via the I/F section 228.

The I/F section 228 is a communication interface section which transmits a setting signal and an instruction signal from the operation control section 32 to each of the sections.

An operation of the diagnostic imaging apparatus 10 as the optical structure observation apparatus of the present embodiment thus configured will be described with use of a flowchart of FIG. 6 with reference to FIGS. 7 to 16.

Figure 6:
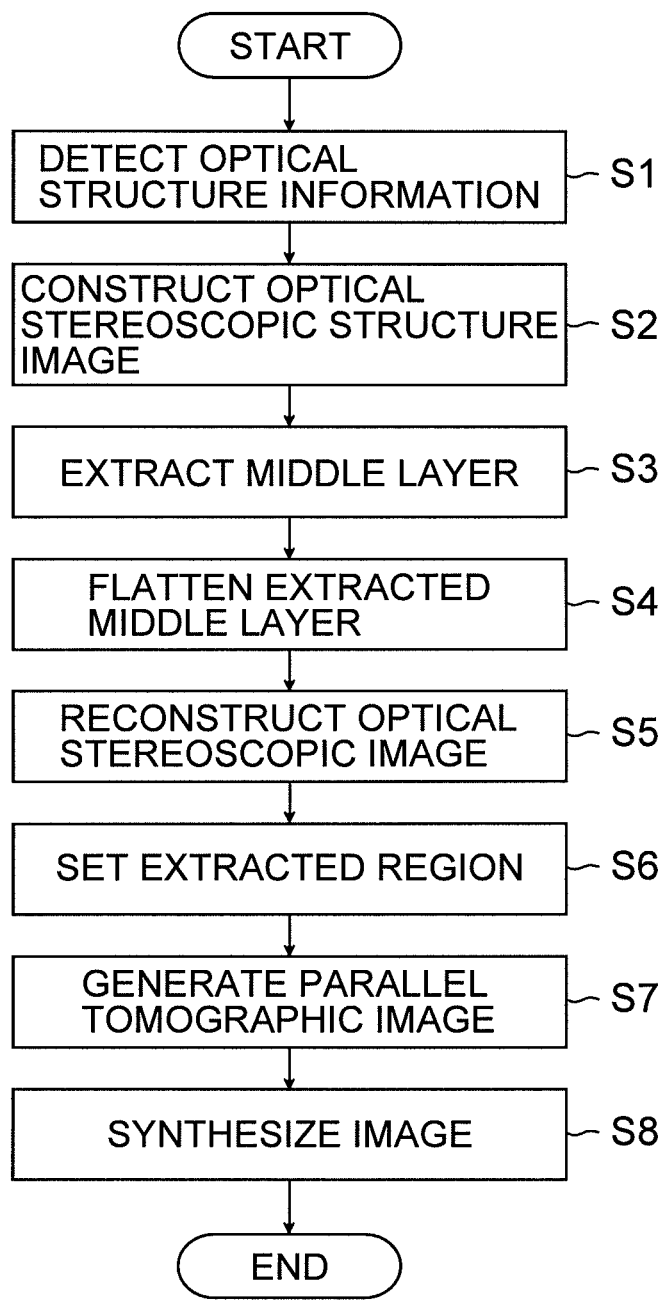
FIG. 6 is a flowchart explaining an operation of the diagnostic imaging apparatus of FIG. 1.

FIG. 6 is the flowchart explaining the operation of the diagnostic imaging apparatus of FIG. 1, and FIGS. 7 to 16 are diagrams for explaining the processing of FIG. 6.

An operator inputs power supply to each of the sections of the endoscope 100, the endoscope processor 200, the light source device 300, the OCT processor 400 and the monitor device 500 for configuring the diagnostic imaging apparatus 10, brings the tip end portion 144 of the insertion section 602 of the OCT probe 600 guided out of the forceps port 156 of the endoscope 100 close to the mucosa of a large intestine (measurement object S), for example, and starts optical scanning by the OCT probe 600.

Figure 7:
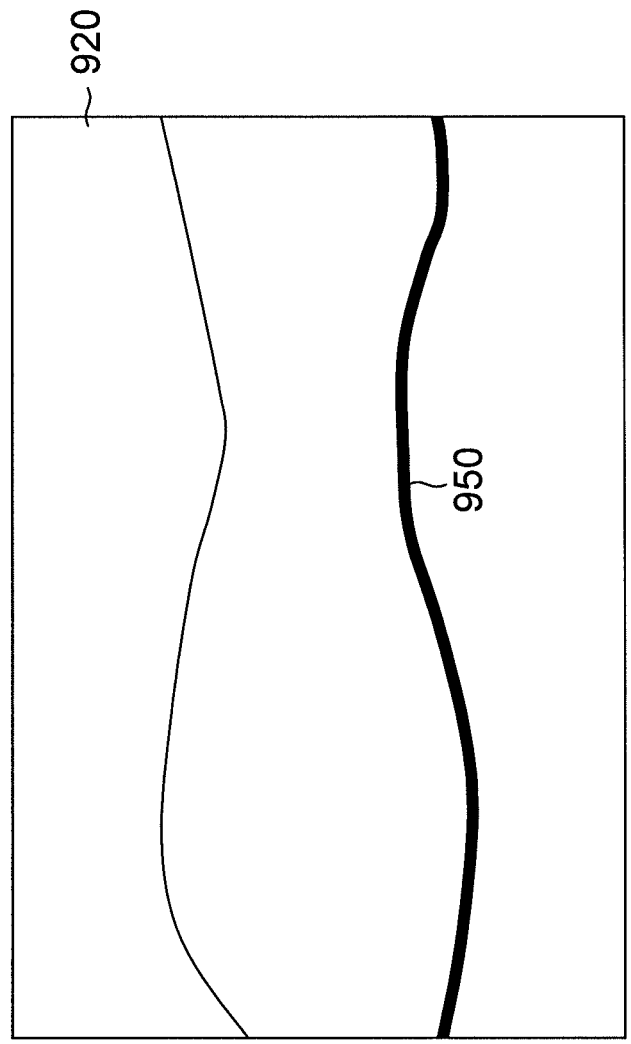
FIG. 7 is a first diagram for explaining processing of FIG. 6.
Figure 8:
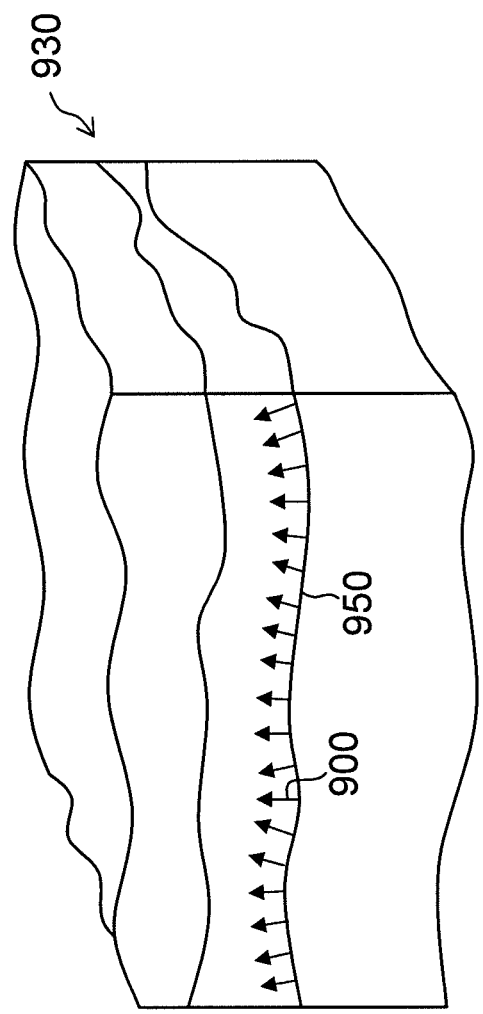
FIG. 8 is a view showing an optical stereoscopic structure image generated by an optical stereoscopic structure image constructing section of FIG. 5.

In the OCT processor 400 of the diagnostic imaging apparatus 10, as shown in FIG. 6, the optical structure information detecting section 220 detects the optical structure information on a scan surface 920 for configuring a tomographic image as shown in FIG. 7 from the coherence signal detected by the coherence light detecting section 20 (step S1), and the optical stereoscopic structure image constructing section 221 generates an optical stereoscopic structure image 930 as shown in FIG. 8 based on the optical structure information detected by the optical structure information detecting section 220 (step S2).

In the optical stereoscopic structure image 930 of FIG. 8, ducts (crypts) are formed substantially vertically on the mucosal layer with a muscular layer of mucosa 950 as a basal plate, and therefore, the orientation of the ducts (crypts) (the arrows 900 in FIG. 8) are random orientations.

At this time, the display control section 227 can output the image of the optical stereoscopic structure image 930 from the optical stereoscopic structure image constructing section 221 to the monitor device 500 by the instruction signal of the operation control section 32 via the I/F section 228.

Next, in the OCT processor 400, the display control section 227 causes the monitor device 500 to display the optical structure information on the scan surface 920 for configuring the optical stereoscopic structure image 930 generated by the optical stereoscopic structure image constructing section 221, and the middle layer extracting section 222 extracts a muscular layer of mucosa 950 as a middle layer in the optical structure information on the scan surface 920 when the measurement object S is the mucosa of a large intestine, for example (step S3).

Figure 9:
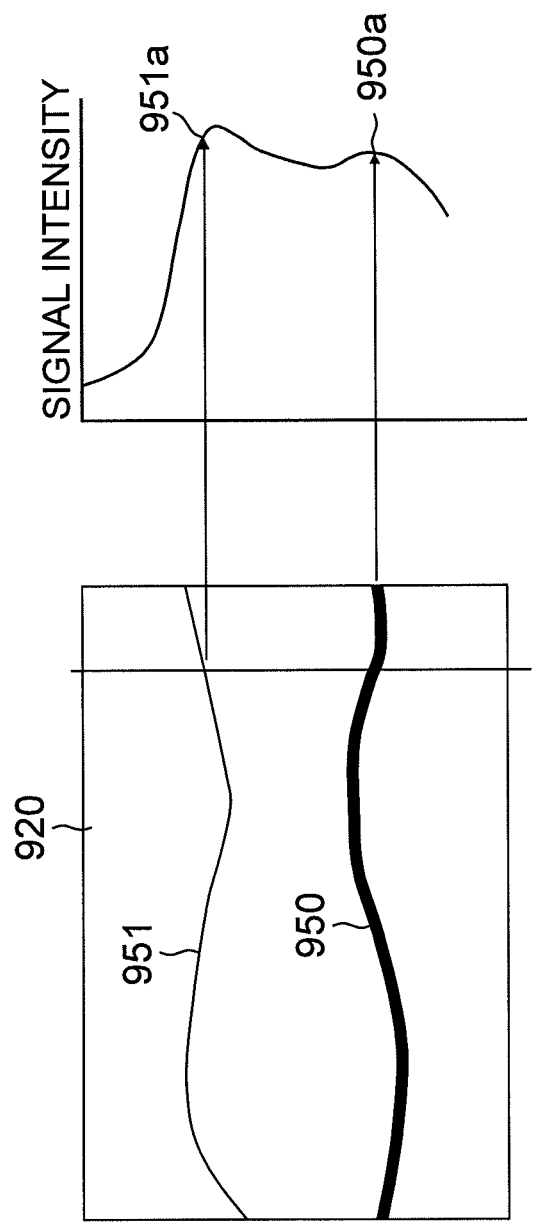
FIG. 9 is a second diagram for explaining the processing of FIG. 6.

In concrete, the middle layer extracting section 222 extracts a muscular layer of mucosa by analyzing the intensity of an image signal. More specifically, the middle layer extracting section 222 determines that in each scan surface 920 for configuring the optical stereoscopic structure image 930, an initial portion 951a with strong image signal intensity is a mucosal surface 951, and a next portion 950a with strong image signal intensity corresponds to the muscular layer of mucosa 950, and extracts the layer position of the muscular layer of mucosa 950, as shown in FIG. 9.

Figure 10:
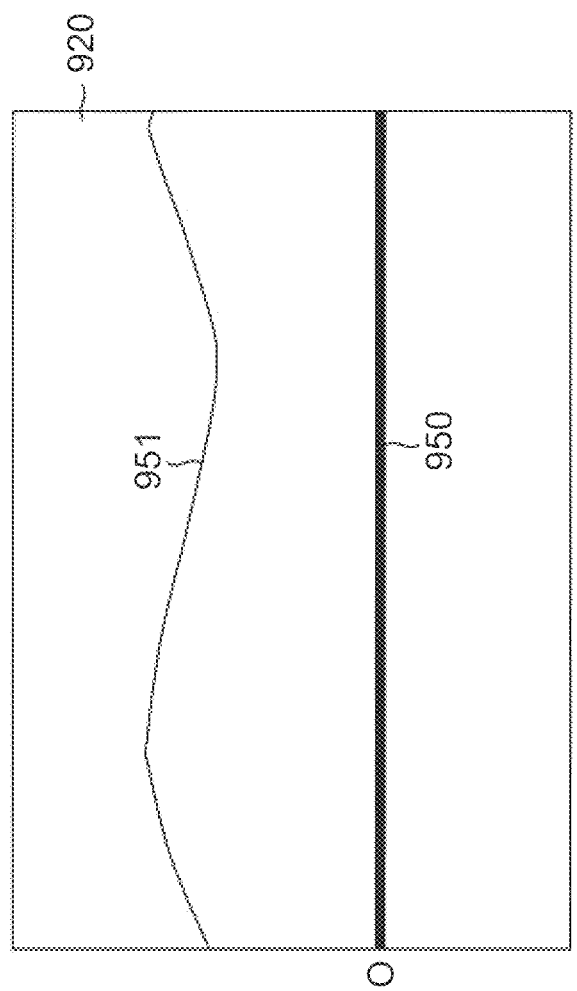
FIG. 10 is a third diagram for explaining the processing of FIG. 6.

Subsequently, in the OCT processor 400, the flattening processing section 223 shifts the optical structure information in the depth direction so as to locate the extracted muscular layer of mucosa 950 in a certain reference position O in order to flatten the layer position of the muscular layer of mucosa 950 extracted by the middle layer extracting section 222, and flattens the muscular layer of mucosa 950 as shown in FIG. 10 (step S4).

Figure 11:
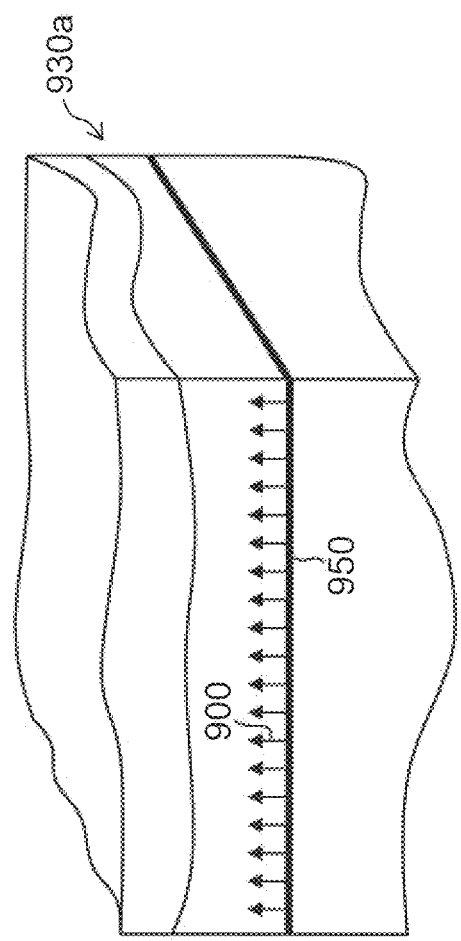
FIG. 11 is a view showing an optical stereoscopic image converted by an optical stereoscopic structure image converting section of FIG. 5.

Subsequently, in the OCT processor 4040, the optical stereoscopic structure image converting section 224 converts the optical stereoscopic structure image 930 into an optical stereoscopic structure image 930a as shown in FIG. 11 so that the muscular layer of mucosa 950 flattened by the flattening processing section 223 becomes the reference surface of the optical stereoscopic structure image (step S5).

At this time, the display control section 227 can output the image of the optical stereoscopic structure image 930a from the optical stereoscopic structure image converting section 224 to the monitor device 500 by the instruction signal of the operation control section 32 via the I/F section 228, and the ducts are formed substantially vertically in the mucosal layer with the flattened muscular layer of mucosa 950 as a basal plate in the optical stereoscopic structure image 930a as shown in FIG. 11. Therefore, the orientations (arrow 900 in FIG. 11) of the ducts (crypts) are regular orientations when the ducts (crypts) are normal. In this manner, the state of the ducts (crypts) can be easily determined visually by the optical stereoscopic structure image 930a.

Figure 12:
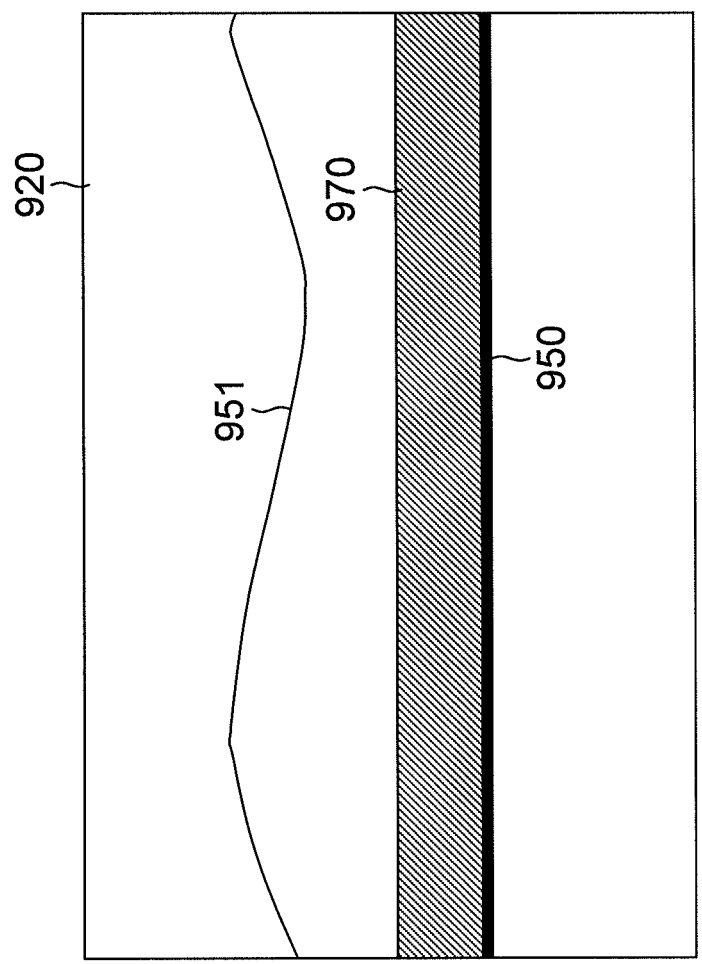
FIG. 12 is a fourth diagram for explaining the processing of FIG. 6.
Figure 13:
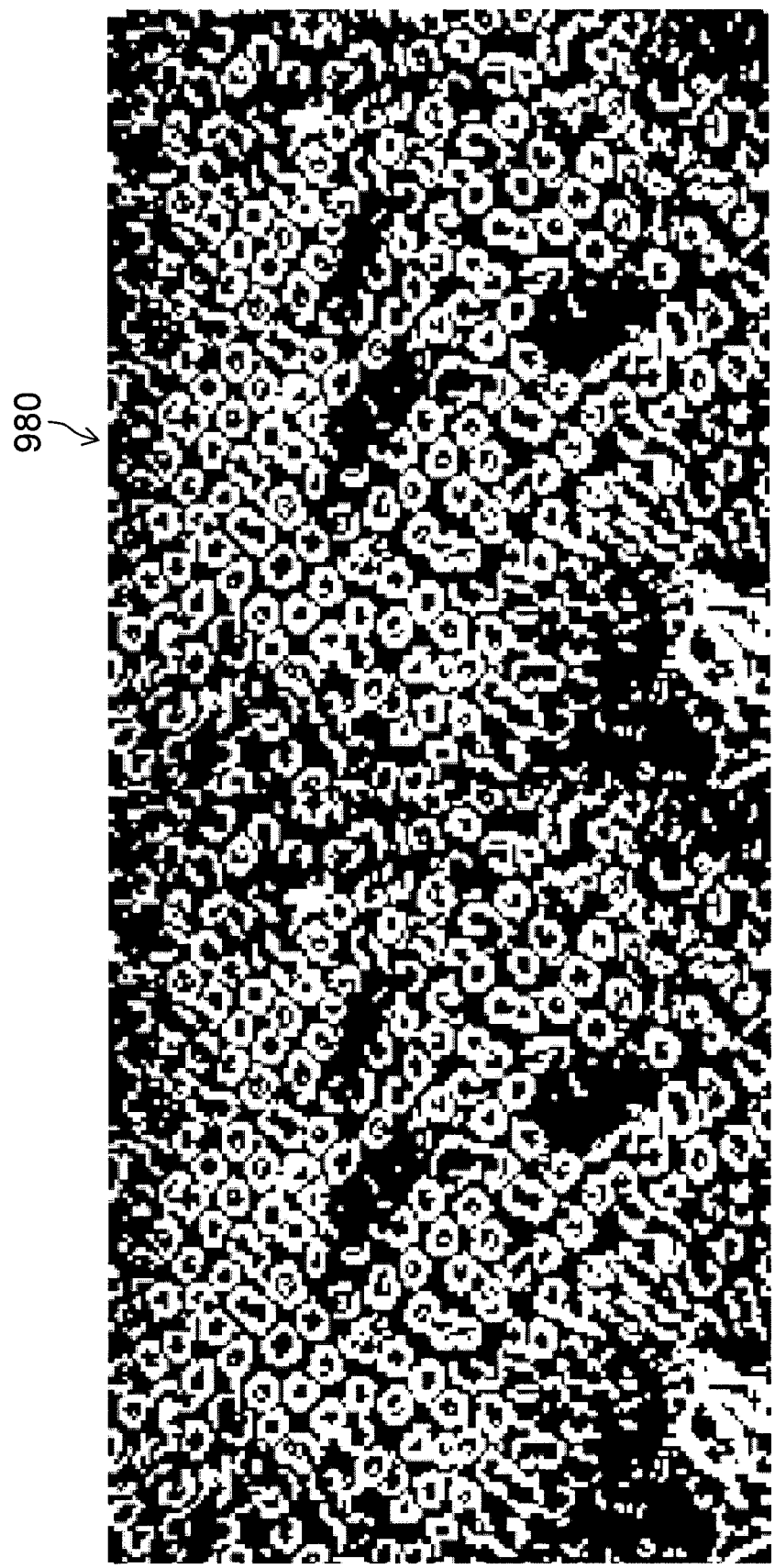
FIG. 13 is a view showing one example of a parallel sectional image of a regularly arranged pit pattern when ducts (crypts) are normal, which is generated by a parallel tomographic image generating section of FIG. 5.

Next, in the OCT processor 400, the display control section 227 causes the monitor device 500 to display the optical structure information on the scan surface 920 for configuring the optical stereoscopic structure image 930a which is converted by the optical stereoscopic structure image converting section 224, and as shown in FIG. 12, in the optical structure information on the scan surface 920, the operation control section 32 sets an extracted region 970 which is in a certain fixed range at an optional height from the muscular layer of mucosa 950 (step S6), the parallel tomographic image generating section 225 integrates the optical structure information of the extracted region 970 along the direction orthogonal to the reference layer, and generates a parallel sectional image 980 which is an integrated image in which a pit pattern appears as shown in FIG. 13 (step S7).

Figure 14:
FIG. 14 is a view showing one example of a parallel sectional image of a random pit pattern in the case of canceration of ducts (crypt), which is generated by the parallel tomographic image generating section of FIG. 5.

At this time, the display control section 227 can output a parallel sectional image 980a from the parallel tomographic image generating section 225 to the monitor device 500 by the instruction signal of the operation control section 32 via the I/F section 228. FIG. 13 shows one example of the parallel sectional image 980 of the regularly arranged pit pattern when the ducts (crypts) are normal. FIG. 14 shows one example of the parallel sectional image 980 of a random pit pattern when the ducts (crypts) have concerted. In this manner, the state of the ducts (crypts) can be also determined visually by the parallel sectional image 980.

Figure 15:
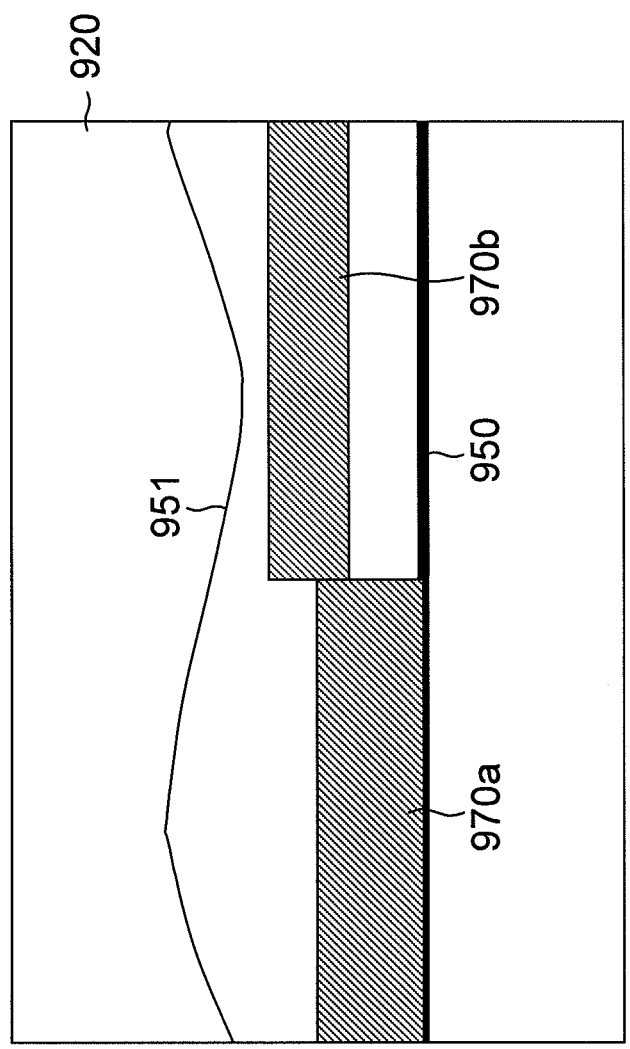
FIG. 15 is a fifth diagram for explaining the processing of FIG. 6.

In steps S6 and S7, as shown in FIG. 15, in the optical structure information on the scan surface 920, the operation control section 32 sets a plurality of extracted regions 970 (two extracted regions 970a and 970b in FIG. 15) in certain fixed ranges at optional heights from the muscular layer of mucosa 950, the parallel tomographic image generating section 225 integrates the optical structure information of a plurality of extracted regions 970 along the direction orthogonal to the reference layer, and can generate a plurality of parallel sectional images 980. In this case, in the OCT processor 400, the image synthesizing section 226 synthesizes a plurality of parallel sectional images 980 which correspond to a plurality of extracted regions and are generated by the parallel tomographic image generating section 225 (step S8).

Figure 16:
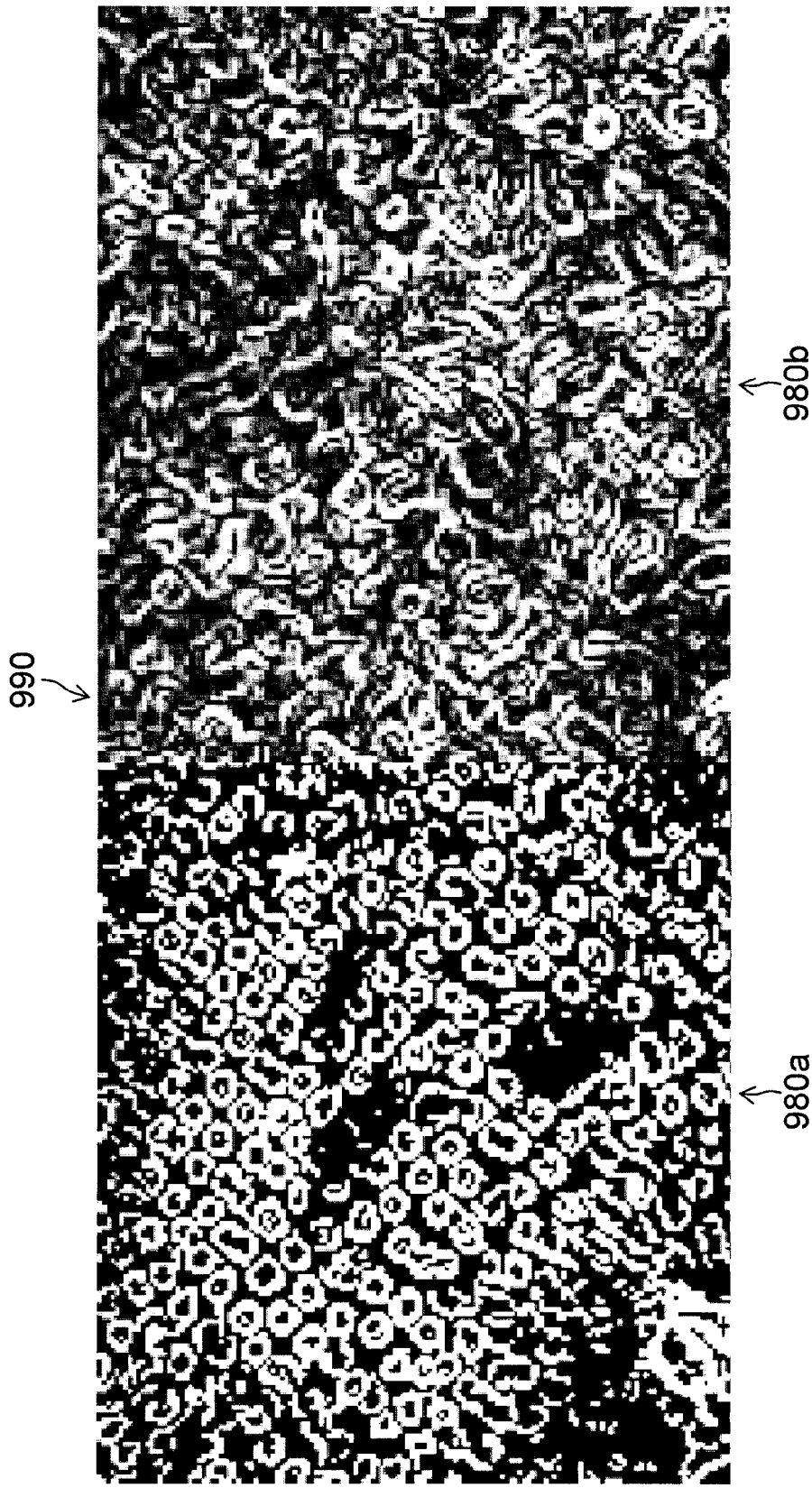
FIG. 16 is a view showing a synthesized image which is made by arranging two parallel sectional images in parallel, and synthesizing the two parallel sectional images, which is generated by an image synthesizing section of FIG. 5.
Figure 17:
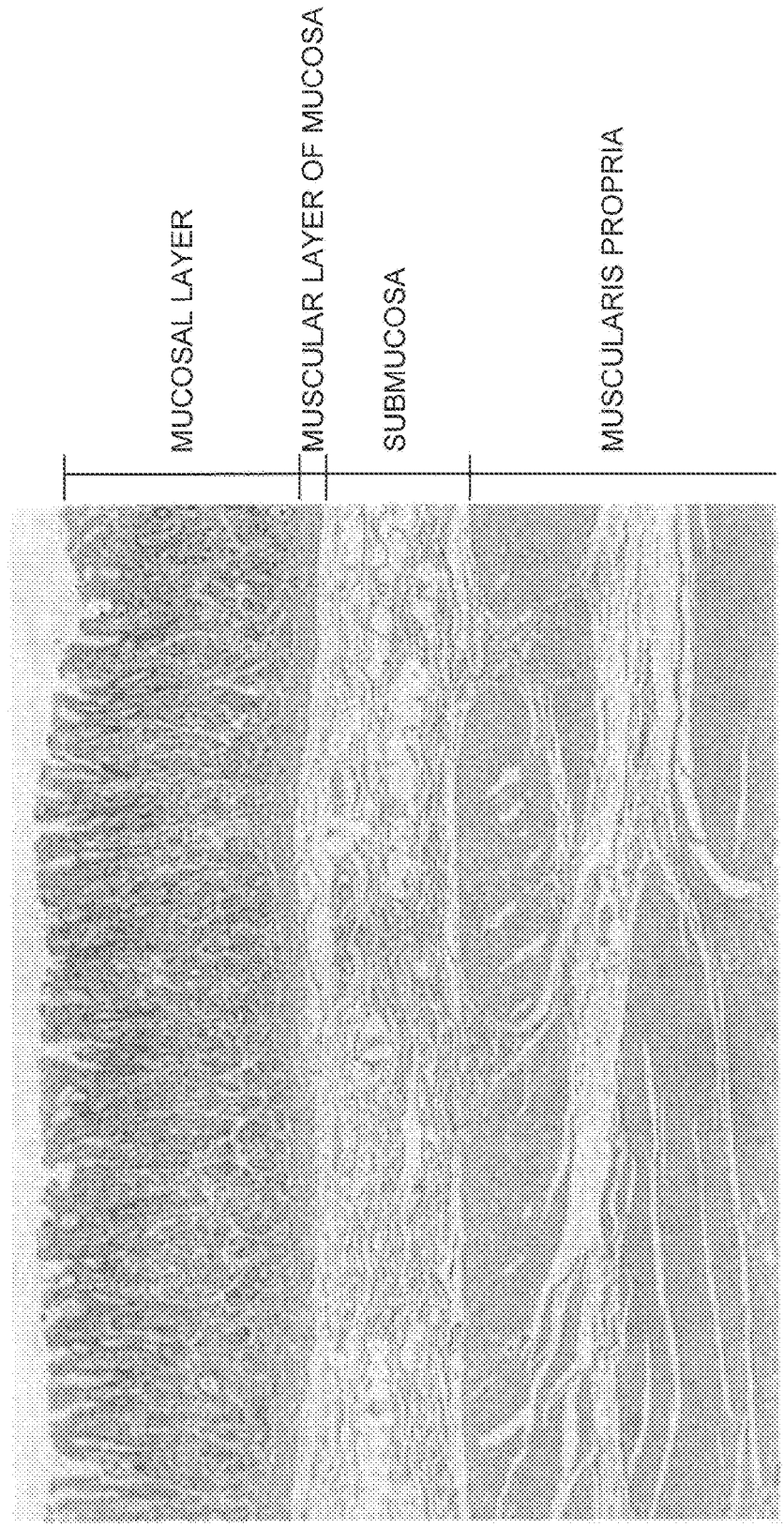
FIG. 17 is a view explaining a structure of a large intestine.
Figure 18:
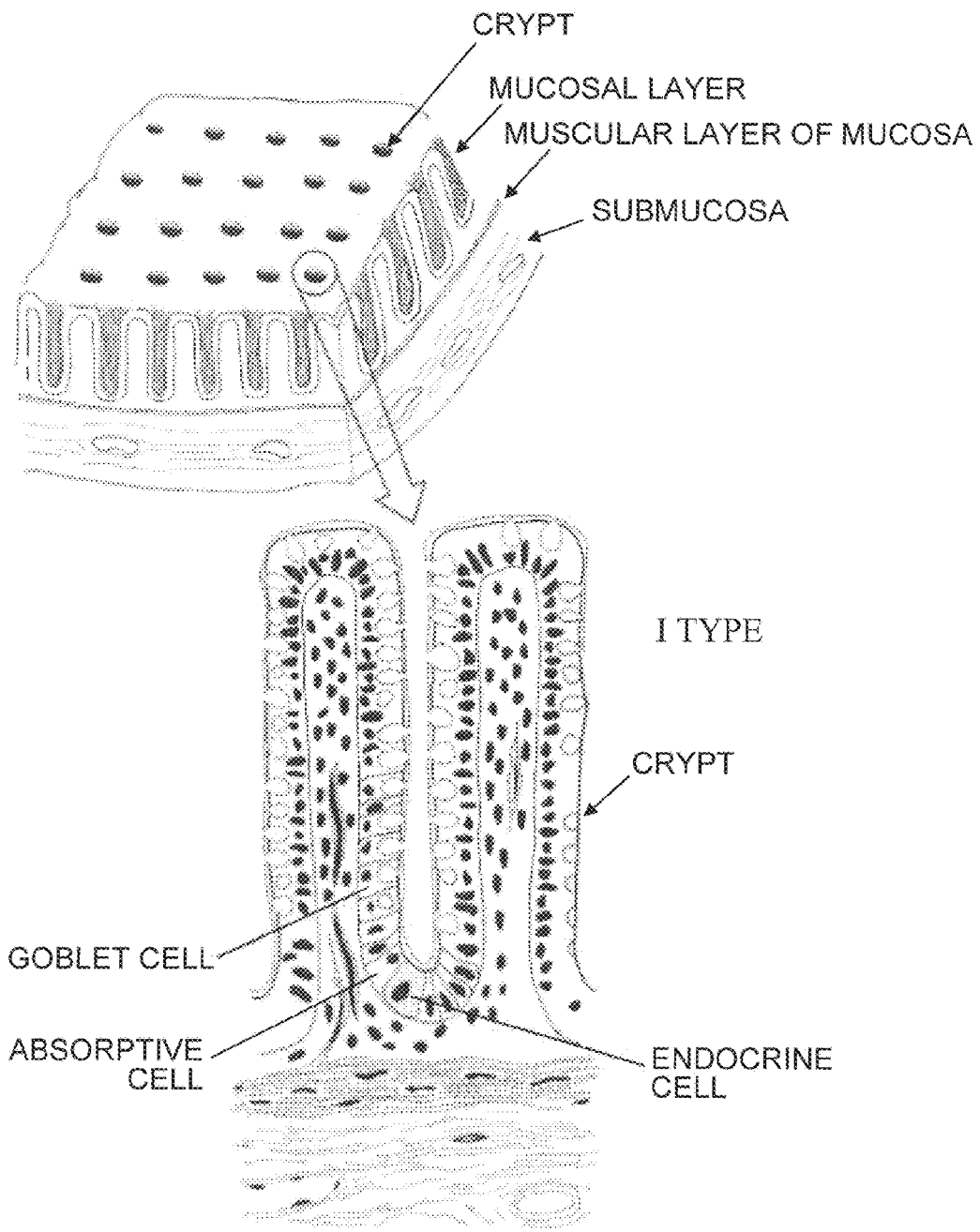
FIG. 18 is a view explaining ducts formed substantially vertically in a mucosal layer with a muscular layer of mucosa of FIG. 17 as a basal plate.
Figure 19:
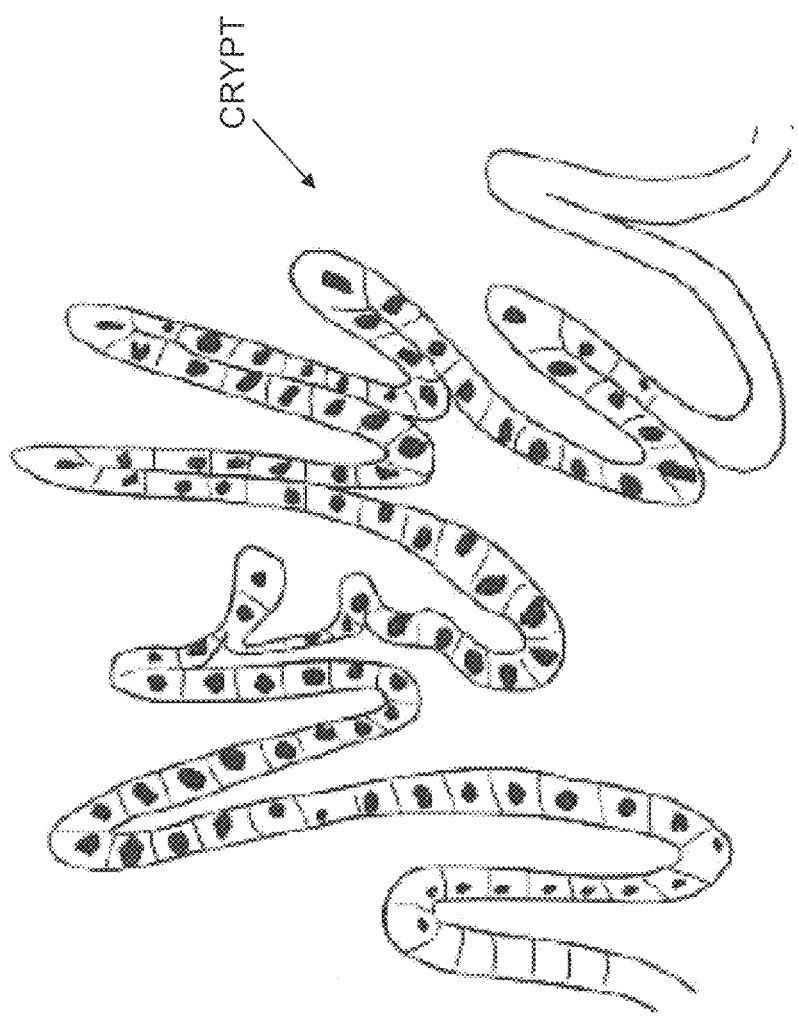
FIG. 19 is a first view showing a deformed state due to canceration of the duct of FIG. 18.
Figure 20:
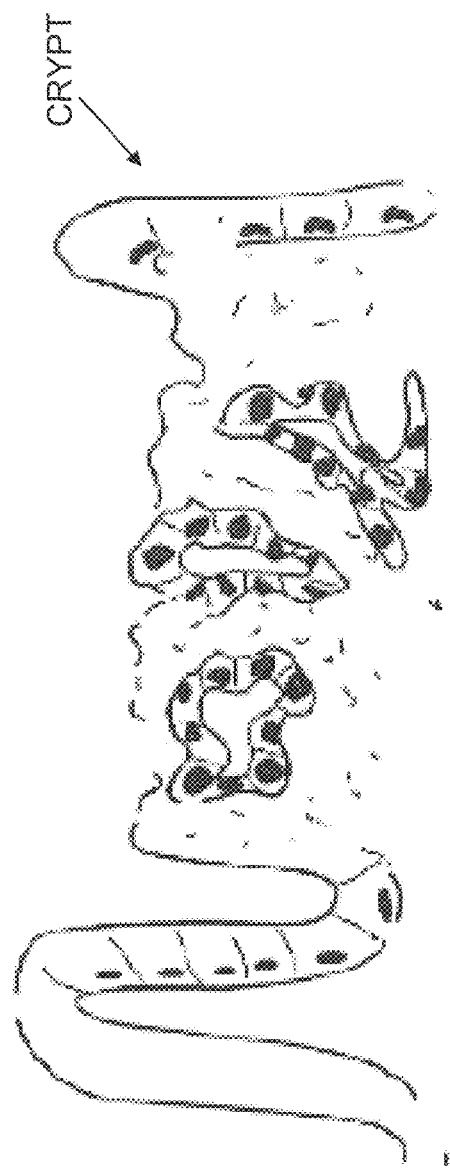
FIG. 20 is a second view showing a deformed state due to canceration of the duct of FIG. 18.

At this time, the display control section 227 can output the synthesized image from the image synthesizing section 226 to the monitor device 500 by the designating signal of the operation control section 32 via the I/F section 228. FIG. 16 shows a synthesized image 990 which is the result that the image synthesizing section 226 synthesizes two parallel sectional images 980a and 980b generated in the two extracted regions 970a and 970b of FIG. 15 by arranging the parallel sectional images 980a and 980b in parallel. In the case of the synthesized image 990, the ducts (crypts) of the region of the parallel sectional image 980a are normal, and the ducts (crypts) of the region of the parallel sectional image 980b show a concretized state.

As shown in FIG. 16, the regularities of the images of the region of the parallel sectional image 980a and that of the parallel sectional image 980b significantly differ, both of them can be compared with each other in the synthesized image 990, and therefore, the state of the ducts (crypts) can be more visually determined.

More specifically, by the synthesized image, the parallel sectional images at the positions at different depths in different places are obtained, synthesized and displayed, or can be displayed by being arranged on the same screen. Further, the parallel sectional images in different integrated ranges in different places are synthesized and displayed, or can be arranged on the same screen and displayed by the synthesized image. In this manner, comparison of regions of interest and comparison of a normal portion and an abnormal portion can be performed easily with high precision. As described above, according to the present embodiment, three-dimensional structures in the depth direction with the muscular layers of mucosa as the centers of organs such as an esophagus, a stomach and an intestine can be analyzed and displayed. For example, the structures of a large intestine duct, an esophagus IPCL (intra epithelial capillary loop) and the like can be three-dimensionally visualized with non-contact. Further, the state of the region of the lesion portion changing in the depth direction can be visually grasped. Therefore, detailed observation of the structures is enabled, and the information which enables more accurate diagnosis can be provided.

The above described present embodiment is applicable to any organ in which the duct structure appears on the mucosal surface, and is applicable to for example, a stomach, a duodenum, a jejunum, an ileum, a colon and a rectum. The present embodiment becomes applicable to an esophagus, a pharynx, a larynx, a bile duct, a pancreatic duct, a bladder, a vagina, a womb and the like characterized by neovascularities appearing on original squamous epitheliums by recognizing the neovascularities. Presence or absence of the pattern peculiar to a neovasculariry is recognized by using a pattern recognizing method, and by color-coding the regions of a normal part and an abnormal part, the abnormal part in the depth direction can be extracted. The optical structure observation apparatus of the present invention is described in detail above, but it goes without saying that the present invention is not limited to the above example, and various improvements and modifications may be made within the scope without departing from the gist of the present invention.

What is claimed is:

1. An optical structure observation apparatus, which acquires a plurality of pieces of optical structure information of a measured object obtained by scanning a scan surface constituted of a first direction, which is a depth direction of the measured object having a layer structure at least including a surface layer and a middle layer, and a second direction orthogonal to the first direction, by using a low coherence light, while shifting a position along a third direction which is a direction orthogonal to the scan surface, and constructs an optical stereoscopic structure image based on a plurality of pieces of the optical structure information which are acquired, comprising:
   a probe which obtains the plurality of pieces of optical structure information and comprises an optical fiber configured to be rotated in a direction of a circumferential direction of the probe and be moved in a longitudinal direction of the probe;
   a middle layer extracting device which extracts the desired middle layer in the measured object from the plurality of pieces of optical structure information configuring the optical stereoscopic structure image;
   a layer flattening device which flattens the middle layer extracted by the middle layer extracting device to be a same flat plane;
   a structure image converting device which reconstructs the optical stereoscopic structure image with the flattened middle layer as a reference layer, and generates a three-dimensional converted optical structure image; and
   a display control device which images and outputs at least the three-dimensional converted optical structure image.

2. The optical structure observation apparatus according to claim 1, further comprising:
   an extracted region setting device which sets an extracted region with a parallel surface located at a desired height parallel with the reference layer as a parallel section, on the three-dimensional converted optical structure image;
   a region information extracting device which extracts the plurality of pieces of optical structure information in the extracted region; and
   a parallel sectional image generating device which generates a parallel sectional image based on the plurality of pieces of optical structure information in the extracted region extracted by the region information extracting device.

3. The optical structure observation apparatus according to claim 2,
   wherein the region information extracting device sets a plurality of extracted regions constituted of different regions having a plurality of parallel surfaces located at a plurality of desired heights parallel with the reference layer as parallel sections respectively, and the parallel sectional image generating device generates a plurality of the parallel sectional images for each of the plurality of extracted regions.

4. The optical structure observation apparatus according to claim 3, further comprising:
   an image synthesizing device which generates a synthesized image with a plurality of the parallel sectional images being synthesized.

5. The optical structure observation apparatus according to claim 4,
   wherein the display control device causes the display device to display the synthesized image.

6. The optical structure observation apparatus according to claim 2,
   wherein the display control device causes the display device to display the parallel sectional image.

7. The optical structure observation apparatus according to claim 2,
   wherein the parallel sectional image generating device generates a parallel sectional image by performing any one processing of integration processing, maximum intensity projection, and minimum intensity projection for the plurality of pieces of optical structure information in the extracted region along a direction orthogonal to the reference layer.

8. The optical structure observation apparatus according to claim 2,
   wherein the parallel sectional image is of a crypt structure or an arrangement pattern of a blood vessel.

9. The optical structure observation apparatus according to claim 1,
   wherein the middle layer is a muscular layer of mucosa or a basal layer.

10. A structure information processing method of an optical structure observation apparatus, which acquires a plurality of pieces of optical structure information of a measured object obtained by scanning a scan surface constituted of a first direction, which is a depth direction of the measured object having a layer structure at least including a surface layer and a middle layer, and a second direction orthogonal to the first direction, by using a low coherence light, while shifting a position along a third direction which is a direction orthogonal to the scan surface, and constructs an optical stereoscopic structure image based on a plurality of pieces of the optical structure information which are acquired, comprising:
    a step of obtaining the plurality of pieces of optical structure information by a probe of the optical structure observation apparatus including an optical fiber configured to be rotated in a direction of a circumferential direction of the probe and be moved in a longitudinal direction of the probe;
    a middle layer extracting step of extracting the middle layer in the measured object from the plurality of pieces of optical structure information configuring the optical stereoscopic structure image;
    a layer flattening step of flattening the middle layer extracted by the middle layer extracting step to be a same flat plane;
    a structure image converting step of reconstructing the optical stereoscopic structure image with the flattened middle layer as a reference layer, and generating a three-dimensional converted optical structure image; and
    a display control step of imaging and outputting at least three-dimensional converted optical structure image.

11. The structure information processing method of an optical structure observation apparatus according to claim 10, further comprising:

an extracted region setting step of setting an extracted region with a parallel surface located at a desired height parallel with the reference layer as a parallel section, on the three-dimensional converted optical structure image;

a region information extracting step of extracting the plurality of pieces of optical structure information in the extracted region; and a parallel sectional image generating step of generating a parallel sectional image based on the plurality of pieces of optical structure information in the extracted region extracted in the region information extracting step.

12. The structure information processing method of an optical structure observation apparatus according to claim 11, wherein the region information extracting step sets a plurality of extracted regions constituted of different regions having a plurality of parallel surfaces located at a plurality of desired heights parallel with the reference layer as parallel sections respectively, and the parallel sectional image generating step generates a plurality of the parallel sectional images for each of the plurality of extracted regions.

13. The structure information processing method of an optical structure observation apparatus according to claim 12, further comprising:

an image synthesizing step of generating a synthesized image with a plurality of the parallel sectional images being synthesized.

14. The structure information processing method of an optical structure observation apparatus according to claim 13, wherein the display control step causes the display device to display the synthesized image.

15. The structure information processing method of an optical structure observation apparatus according to claim 11, wherein the display control step causes the display device to display the parallel sectional image.

16. The structure information processing method of an optical structure observation apparatus according to claim 11, wherein the parallel sectional image generating step generates a parallel sectional image by performing any one processing of integration processing, maximum intensity projection, and minimum intensity projection for the plurality of pieces of optical structure information in the extracted region along a direction orthogonal to the reference layer.

17. The structure information processing method of an optical structure observation apparatus according to claim 11, wherein the parallel sectional image is of a crypt structure or an arrangement pattern of a blood vessel.

18. The structure information processing method of an optical structure observation apparatus according to claim 10, wherein the middle layer is a muscular layer of mucosa or a basal layer.

* * * * *